(12) United States Patent
Kidd et al.

(10) Patent No.: US 10,537,713 B2
(45) Date of Patent: Jan. 21, 2020

(54) REMOTE MANIPULATOR DEVICE

(75) Inventors: Brian L. Kidd, St. Louis, MO (US);
Nathan Kastelein, St. Louis, MO (US)

(73) Assignee: Stereotaxis, Inc., St. Louis, MO (US)

( * ) Notice: Subject to any disclaimer, the term of this patent is extended or adjusted under 35 U.S.C. 154(b) by 539 days.

(21) Appl. No.: 12/954,648

(22) Filed: Nov. 25, 2010

(65) Prior Publication Data

US 2011/0130718 A1     Jun. 2, 2011

Related U.S. Application Data

(63) Continuation-in-part of application No. 12/786,833, filed on May 25, 2010, now abandoned.

(Continued)

(51) Int. Cl.
*A61M 25/092*     (2006.01)
*A61M 25/01*     (2006.01)

(52) U.S. Cl.
CPC ................ *A61M 25/0133* (2013.01)

(58) Field of Classification Search
CPC . A61B 19/22; A61B 19/20; A61B 2019/2223; A61B 2019/2207;
(Continued)

(56) References Cited

U.S. PATENT DOCUMENTS 5,353,807 A     10/1994     DeMarco
5,553,198 A     9/1996     Wang et al.

(Continued)

FOREIGN PATENT DOCUMENTS

EP     0 839 547     9/2003
JP     2002522105     7/2002 ............... A61B 8/12
(Continued)

OTHER PUBLICATIONS

Magnetic Manipulation Instrumentation for Medical Physics Research Authors: G. T. Gillies, r. C. Ritter, W. C. Broaddus, M. S. Grady, M. A. Howard, III, R. G. McNeil 1994 American Institute of Physics Rev. Sci. Instrum. vol. 65, No. 3, Mar. 1994 pp. 533-562.

(Continued)

*Primary Examiner* — Todd J Scherbel
(74) *Attorney, Agent, or Firm* — Harness, Dickey & Pierce, P.L.C.; Bryan K. Wheelock

(57) ABSTRACT

A system for operating a catheter having a distal end adapted to be navigated in the body, and a proximal end having a handle with a translatable control and a rotatable control for acting on the distal end of the device includes a support for receiving and engaging the handle of the catheter; a translation mechanism for advancing and retracting the support to advance and retract a catheter whose handle is received in the support; a rotation mechanism for rotating the support to rotate a catheter whose handle is received in the support; a translation operator for engaging the translatable control of a catheter whose handle is received in the support and operating the translatable control to act on the distal end of the device; and a rotation operator for engaging the rotatable control of a catheter whose handle is received in the support and operating the rotatable control to act on the distal end of the device.

3 Claims, 29 Drawing Sheets

Related U.S. Application Data

(60) Provisional application No. 61/180,926, filed on May 25, 2009.

(58) Field of Classification Search
CPC ...... A61B 2019/2211; A61B 2019/223; A61B 2019/2215–2219; A61B 2019/2226; A61B 2019/501; A61B 19/2203; A61B 19/201; A61B 2017/3409; A61B 2017/22075; A61B 1/01; A61M 25/0113; A61M 25/0105; A61M 25/0116; Y10T 74/20305–20335; B25J 9/102; B25J 9/126; B25J 15/0213
USPC ........................................ 606/130; 604/95.01
See application file for complete search history.

(56) References Cited

U.S. PATENT DOCUMENTS

| | | |
|---|---|---|
| 5,654,864 A | 8/1997 | Ritter et al. |
| 5,707,335 A | 1/1998 | Howard et al. |
| 5,779,694 A | 7/1998 | Howard et al. |
| 5,814,038 A * | 9/1998 | Jensen ............... A61B 19/2203 403/316 |
| 5,931,818 A | 8/1999 | Werp et al. |
| 6,014,580 A | 1/2000 | Blume et al. |
| 6,015,414 A | 1/2000 | Werp et al. |
| 6,128,174 A | 10/2000 | Ritter et al. |
| 6,148,823 A | 11/2000 | Hastings |
| 6,152,933 A | 11/2000 | Werp et al. |
| 6,157,853 A | 12/2000 | Blume et al. |
| 6,212,419 B1 | 4/2001 | Blume et al. |
| 6,241,671 B1 | 6/2001 | Ritter et al. |
| 6,272,370 B1 | 8/2001 | Gillies et al. |
| 6,292,678 B1 | 9/2001 | Hall et al. |
| 6,296,604 B1 | 10/2001 | Garibaldi et al. |
| 6,298,257 B1 | 10/2001 | Hall et al. |
| 6,298,259 B1 | 10/2001 | Kucharczyk et al. |
| 6,304,768 B1 | 10/2001 | Blume et al. |
| 6,311,082 B1 | 10/2001 | Creighton, IV et al. |
| 6,315,709 B1 | 11/2001 | Garibaldi et al. |
| 6,330,467 B1 | 12/2001 | Creighton, IV et al. |
| 6,352,363 B1 | 3/2002 | Munger et al. |
| 6,364,823 B1 | 4/2002 | Garibaldi et al. |
| 6,375,606 B1 | 4/2002 | Garibaldi et al. |
| 6,385,472 B1 | 5/2002 | Hall et al. |
| 6,401,723 B1 | 6/2002 | Garibaldi et al. |
| 6,428,551 B1 | 8/2002 | Hall et al. |
| 6,459,924 B1 | 10/2002 | Creighton, IV et al. |
| 6,474,377 B1 * | 11/2002 | Van De Mortel .......... 144/24.13 |
| 6,475,223 B1 | 11/2002 | Werp et al. |
| 6,505,062 B1 | 1/2003 | Ritter et al. |
| 6,507,751 B2 | 1/2003 | Blume et al. |
| 6,522,909 B1 | 2/2003 | Garibaldi et al. |
| 6,524,303 B1 | 2/2003 | Garibaldi |
| 6,527,782 B2 | 3/2003 | Hogg et al. |
| 6,529,761 B2 | 3/2003 | Creighton, IV et al. |
| 6,537,196 B1 | 3/2003 | Creighton, IV et al. |
| 6,542,766 B2 | 4/2003 | Hall et al. |
| 6,562,019 B1 | 5/2003 | Sell |
| 6,630,879 B1 | 10/2003 | Creighton, IV et al. |
| 6,662,034 B2 | 12/2003 | Segner et al. |
| 6,677,752 B1 | 1/2004 | Creighton, IV et al. |
| 6,702,804 B1 | 3/2004 | Ritter et al. |
| 6,733,511 B2 | 5/2004 | Hall et al. |
| 6,740,103 B2 | 5/2004 | Hall et al. |
| 6,755,816 B2 | 6/2004 | Ritter et al. |
| 6,786,219 B2 | 9/2004 | Garibaldi et al. |
| 6,817,364 B2 | 11/2004 | Garibaldi et al. |
| 6,834,201 B2 | 12/2004 | Gillies et al. |
| 6,902,528 B1 | 6/2005 | Garibaldi et al. |
| 6,911,026 B1 | 6/2005 | Hall et al. |
| 6,940,379 B2 | 9/2005 | Creighton |
| 6,968,846 B2 | 11/2005 | Viswanathan |
| 6,975,197 B2 | 12/2005 | Creighton, IV |
| 6,980,843 B2 | 12/2005 | Eng et al. |
| 7,008,418 B2 | 3/2006 | Hall et al. |
| 7,010,338 B2 | 3/2006 | Ritter et al. |
| 7,017,584 B2 | 3/2006 | Garibaldi et al. |
| 7,019,610 B2 | 3/2006 | Creighton, IV et al. |
| 7,020,512 B2 | 3/2006 | Ritter et al. |
| 7,066,924 B1 | 6/2006 | Garibaldi et al. |
| 7,137,976 B2 | 11/2006 | Ritter et al. |
| 7,161,453 B2 | 1/2007 | Creighton, IV |
| 7,189,198 B2 | 3/2007 | Harburn et al. |
| 7,190,819 B2 | 3/2007 | Viswanathan |
| 7,211,082 B2 | 5/2007 | Hall et al. |
| 7,248,914 B2 | 7/2007 | Hastings et al. |
| 7,264,584 B2 | 9/2007 | Ritter et al. |
| 7,276,044 B2 | 10/2007 | Ferry et al. |
| 7,286,034 B2 | 10/2007 | Creighton |
| 7,305,263 B2 | 12/2007 | Creighton, IV |
| 7,313,429 B2 | 12/2007 | Creighton, IV et al. |
| 7,331,967 B2 * | 2/2008 | Lee ............... A61B 19/2203 600/407 |
| 7,341,063 B2 | 3/2008 | Garibaldi et al. |
| 7,346,379 B2 | 3/2008 | Eng et al. |
| 7,389,778 B2 | 6/2008 | Sabo et al. |
| 7,416,335 B2 | 8/2008 | Munger |
| 7,495,537 B2 | 2/2009 | Tunay |
| 7,505,615 B2 | 3/2009 | Viswanathan |
| 7,516,416 B2 | 4/2009 | Viswanathan et al. |
| 7,537,570 B2 | 5/2009 | Kastelein |
| 7,540,288 B2 | 6/2009 | Viswanathan et al. |
| 7,540,866 B2 | 6/2009 | Viswanathan et al. |
| 7,543,239 B2 | 6/2009 | Viswanathan et al. |
| 7,555,331 B2 | 6/2009 | Viswanathan |
| 7,567,233 B2 | 7/2009 | Garibaldi et al. |
| 7,603,905 B2 | 10/2009 | Creighton, IV |
| 7,623,736 B2 | 11/2009 | Viswanathan |
| 7,625,382 B2 | 12/2009 | Werp et al. |
| 7,627,361 B2 | 12/2009 | Viswanathan |
| 7,630,752 B2 | 12/2009 | Viswanathan |
| 7,635,342 B2 | 12/2009 | Ferry et al. |
| 7,657,075 B2 | 2/2010 | Viswanathan |
| 7,662,126 B2 | 2/2010 | Creighton, IV |
| 7,690,619 B2 | 4/2010 | Wolfersberger |
| 7,708,696 B2 | 5/2010 | Ritter et al. |
| 7,742,803 B2 | 6/2010 | Viswanathan et al. |
| 7,747,960 B2 | 6/2010 | Garibaldi et al. |
| 7,751,867 B2 | 7/2010 | Viswanathan et al. |
| 7,756,308 B2 | 7/2010 | Viswanathan |
| 7,757,694 B2 | 7/2010 | Ritter et al. |
| 7,761,133 B2 | 7/2010 | Viswanathan et al. |
| 7,766,856 B2 | 8/2010 | Ferry et al. |
| 7,769,428 B2 | 8/2010 | Viswanathan et al. |
| 7,769,444 B2 | 8/2010 | Pappone |
| 7,771,415 B2 | 8/2010 | Ritter et al. |
| 7,771,437 B2 | 8/2010 | Hogg et al. |
| 7,772,950 B2 | 8/2010 | Tunay |
| 7,774,046 B2 | 8/2010 | Werp et al. |
| 7,815,580 B2 | 10/2010 | Viswanathan |
| 7,818,076 B2 | 10/2010 | Viswanathan |
| 7,831,294 B2 | 11/2010 | Viswanathan |
| 7,853,306 B2 | 12/2010 | Viswanathan et al. |
| 7,892,233 B2 | 2/2011 | Hall et al. |
| 7,927,310 B2 * | 4/2011 | Bencteux et al. ........ 604/165.02 |
| 7,961,924 B2 | 6/2011 | Viswanathan |
| 7,961,926 B2 | 6/2011 | Viswanathan |
| 7,966,059 B2 | 6/2011 | Creighton, IV et al. |
| 7,983,733 B2 | 7/2011 | Viswananthan |
| 7,998,020 B2 | 8/2011 | Kidd et al. |
| 8,024,024 B2 | 9/2011 | Viswanathan et al. |
| 8,046,049 B2 * | 10/2011 | Govari ............... A61B 19/2203 600/407 |
| 8,060,184 B2 | 11/2011 | Hastings et al. |
| 8,088,129 B2 | 1/2012 | Werp et al. |
| 8,202,244 B2 * | 6/2012 | Cohen et al. .............. 604/95.01 |
| 2001/0038683 A1 | 11/2001 | Ritter et al. |
| 2001/0053879 A1 * | 12/2001 | Mills ................... A61B 19/201 600/417 |
| 2002/0019644 A1 | 2/2002 | Hastings et al. |
| 2002/0072704 A1 * | 6/2002 | Mansouri-Ruiz .... A61B 8/4461 604/95.01 |

(56) References Cited

U.S. PATENT DOCUMENTS

| | | |
|---|---|---|
| 2002/0100486 A1 | 8/2002 | Creighton, IV et al. |
| 2003/0208207 A1 | 11/2003 | Layer |
| 2004/0006301 A1 | 1/2004 | Sell et al. |
| 2004/0019447 A1 | 1/2004 | Shachar |
| 2004/0030244 A1 | 2/2004 | Garibaldi et al. |
| 2004/0064153 A1 | 4/2004 | Creighton, IV et al. |
| 2004/0133130 A1 | 7/2004 | Ferry et al. |
| 2004/0147829 A1 | 7/2004 | Segner et al. |
| 2004/0157082 A1 | 8/2004 | Ritter et al. |
| 2004/0158972 A1 | 8/2004 | Creighton, IV et al. |
| 2004/0186376 A1 | 9/2004 | Hogg et al. |
| 2004/0260172 A1 | 12/2004 | Ritter et al. |
| 2004/0267106 A1 | 12/2004 | Segner et al. |
| 2005/0004585 A1 | 1/2005 | Hall et al. |
| 2005/0020911 A1 | 1/2005 | Viswanathan et al. |
| 2005/0021063 A1 | 1/2005 | Hall et al. |
| 2005/0033162 A1 | 2/2005 | Garibaldi et al. |
| 2005/0065435 A1 | 3/2005 | Rauch et al. |
| 2005/0096589 A1 | 5/2005 | Shachar |
| 2005/0113812 A1 | 5/2005 | Viswanathan et al. |
| 2005/0119556 A1 | 6/2005 | Gillies et al. |
| 2005/0119687 A1 | 6/2005 | Dacey, Jr. et al. |
| 2005/0182315 A1 | 8/2005 | Ritter et al. |
| 2005/0203382 A1* | 9/2005 | Govari ............... A61B 19/2203 600/424 |
| 2005/0256398 A1 | 11/2005 | Hastings et al. |
| 2005/0261633 A1 | 11/2005 | Khalaj |
| 2005/0273130 A1 | 12/2005 | Sell |
| 2006/0025675 A1 | 2/2006 | Viswanathan et al. |
| 2006/0025679 A1 | 2/2006 | Viswanathan et al. |
| 2006/0025719 A1 | 2/2006 | Viswanathan et al. |
| 2006/0036163 A1 | 2/2006 | Viswanathan |
| 2006/0041181 A1 | 2/2006 | Viswanathan et al. |
| 2006/0041245 A1* | 2/2006 | Ferry ................. A61B 1/00133 604/510 |
| 2006/0094956 A1 | 5/2006 | Viswanathan |
| 2006/0114088 A1 | 6/2006 | Shachar |
| 2006/0116633 A1 | 6/2006 | Shachar |
| 2006/0144407 A1 | 7/2006 | Aliberto et al. |
| 2006/0144408 A1 | 7/2006 | Ferry |
| 2006/0161136 A1* | 7/2006 | Anderson ............... A61B 19/26 606/1 |
| 2006/0270948 A1 | 11/2006 | Viswanathan et al. |
| 2006/0278248 A1 | 12/2006 | Viswanathan |
| 2006/0282150 A1* | 12/2006 | Olson et al. .................. 623/1.11 |
| 2007/0016010 A1 | 1/2007 | Creighton, IV et al. |
| 2007/0016131 A1 | 1/2007 | Munger et al. |
| 2007/0021731 A1 | 1/2007 | Garibaldi et al. |
| 2007/0021742 A1 | 1/2007 | Viswanathan |
| 2007/0021744 A1 | 1/2007 | Creighton, IV |
| 2007/0032746 A1 | 2/2007 | Sell |
| 2007/0038065 A1 | 2/2007 | Creighton, IV |
| 2007/0038074 A1 | 2/2007 | Ritter et al. |
| 2007/0040670 A1 | 2/2007 | Viswanathan |
| 2007/0043455 A1 | 2/2007 | Viswanathan et al. |
| 2007/0049909 A1 | 3/2007 | Munger |
| 2007/0055124 A1 | 3/2007 | Viswanathan et al. |
| 2007/0055291 A1* | 3/2007 | Birkmeyer ........... A61B 19/201 606/130 |
| 2007/0060829 A1 | 3/2007 | Pappone |
| 2007/0060916 A1 | 3/2007 | Pappone |
| 2007/0060962 A1 | 3/2007 | Pappone |
| 2007/0060992 A1 | 3/2007 | Pappone |
| 2007/0062546 A1 | 3/2007 | Viswanathan et al. |
| 2007/0062547 A1 | 3/2007 | Pappone |
| 2007/0123070 A1* | 5/2007 | Bencteux ........................ 439/78 |
| 2007/0123964 A1 | 5/2007 | Davies et al. |
| 2007/0149946 A1 | 6/2007 | Viswanathan |
| 2007/0161882 A1 | 7/2007 | Pappone |
| 2007/0167720 A1 | 7/2007 | Viswanathan |
| 2007/0179492 A1 | 8/2007 | Pappone |
| 2007/0197899 A1 | 8/2007 | Ritter et al. |
| 2007/0197906 A1 | 8/2007 | Ritter |
| 2007/0225558 A1* | 9/2007 | Hauck .................. A61B 5/6885 600/111 |
| 2007/0225589 A1 | 9/2007 | Viswanathan |
| 2007/0233044 A1* | 10/2007 | Wallace ............... A61B 5/6885 604/528 |
| 2007/0250041 A1 | 10/2007 | Werp |
| 2007/0270686 A1 | 11/2007 | Ritter et al. |
| 2008/0004595 A1 | 1/2008 | Viswanthan |
| 2008/0006280 A1 | 1/2008 | Alberto et al. |
| 2008/0009791 A1* | 1/2008 | Cohen et al. ............... 604/95.01 |
| 2008/0015427 A1 | 1/2008 | Kastelein et al. |
| 2008/0015670 A1 | 1/2008 | Pappone |
| 2008/0016677 A1 | 1/2008 | Creighton, IV |
| 2008/0016678 A1 | 1/2008 | Creighton, IV et al. |
| 2008/0039705 A1 | 2/2008 | Viswanathan |
| 2008/0039830 A1 | 2/2008 | Munger et al. |
| 2008/0045892 A1* | 2/2008 | Ferry .................. A61M 25/0113 604/95.01 |
| 2008/0058608 A1 | 3/2008 | Garibaldi et al. |
| 2008/0058609 A1 | 3/2008 | Garibaldi et al. |
| 2008/0059598 A1 | 3/2008 | Garibaldi et al. |
| 2008/0064933 A1 | 3/2008 | Garibaldi et al. |
| 2008/0065061 A1 | 3/2008 | Viswanathan |
| 2008/0077007 A1 | 3/2008 | Hastings et al. |
| 2008/0092993 A1 | 4/2008 | Creighton, IV |
| 2008/0097200 A1 | 4/2008 | Blume et al. |
| 2008/0114335 A1 | 5/2008 | Flickinger et al. |
| 2008/0119824 A1* | 5/2008 | Weitzner .......... A61B 17/12045 604/523 |
| 2008/0132910 A1 | 6/2008 | Pappone |
| 2008/0161790 A1* | 7/2008 | Dando et al. .................... 606/41 |
| 2008/0200913 A1 | 8/2008 | Viswanathan |
| 2008/0208912 A1 | 8/2008 | Garibaldi |
| 2008/0228065 A1 | 9/2008 | Viswanathan et al. |
| 2008/0228068 A1 | 9/2008 | Viswanathan et al. |
| 2008/0243064 A1* | 10/2008 | Stahler ............... A61B 19/2203 604/95.01 |
| 2008/0287909 A1 | 11/2008 | Viswanathan et al. |
| 2008/0294232 A1 | 11/2008 | Viswanathan |
| 2008/0312673 A1 | 12/2008 | Viswanathan et al. |
| 2008/0319303 A1 | 12/2008 | Sabo et al. |
| 2009/0012821 A1 | 1/2009 | Besson et al. |
| 2009/0054835 A1* | 2/2009 | Anderson ......... A61M 25/0136 604/95.01 |
| 2009/0062646 A1 | 3/2009 | Creighton et al. |
| 2009/0082722 A1* | 3/2009 | Munger et al. ............ 604/95.01 |
| 2009/0105579 A1 | 4/2009 | Garibaldi |
| 2009/0105639 A1* | 4/2009 | Weitzner et al. .......... 604/95.01 |
| 2009/0131798 A1 | 5/2009 | Minar et al. |
| 2009/0131927 A1 | 5/2009 | Kastelein et al. |
| 2009/0138009 A1 | 5/2009 | Viswanathan et al. |
| 2009/0177037 A1 | 7/2009 | Sabo et al. |
| 2009/0306643 A1 | 12/2009 | Pappone et al. |
| 2010/0063385 A1 | 3/2010 | Garibaldi et al. |
| 2010/0069733 A1 | 3/2010 | Kastelein et al. |
| 2010/0097315 A1 | 4/2010 | Garibaldi et al. |
| 2010/0137706 A1 | 6/2010 | Viswanathan |
| 2010/0163061 A1 | 7/2010 | Creighton |
| 2010/0168549 A1 | 7/2010 | Pappone |
| 2010/0174234 A1 | 7/2010 | Werp et al. |
| 2010/0185212 A1* | 7/2010 | Sholev .................. A61B 19/22 606/130 |
| 2010/0222669 A1 | 9/2010 | Flickinger et al. |
| 2010/0298845 A1 | 11/2010 | Kidd et al. |
| 2010/0305502 A1* | 12/2010 | Ferry et al. ............... 604/95.01 |
| 2011/0022029 A1 | 1/2011 | Viswanathan |
| 2011/0028894 A1* | 2/2011 | Foley et al. ............... 604/95.01 |
| 2011/0028989 A1 | 2/2011 | Ritter et al. |
| 2011/0033100 A1 | 2/2011 | Viswanathan |
| 2011/0040150 A1* | 2/2011 | Govari et al. ................ 600/117 |
| 2011/0046618 A1 | 2/2011 | Minar et al. |
| 2011/0087237 A1 | 4/2011 | Viswanathan |

(56) References Cited

U.S. PATENT DOCUMENTS

2011/0130718 A1    6/2011   Kidd et al.
2011/0152712 A1    6/2011   Cao et al.

FOREIGN PATENT DOCUMENTS

| JP | 2007527296   | 9/2007  | ............ A61B 18/12 |
| JP | 2008513057 A | 5/2008  |                         |
| JP | 2008264557   | 11/2008 | ............ A61M 25/01 |

OTHER PUBLICATIONS

International Search Report and Written Opinion for corresponding PCT/US2010/036052 dated Jul. 28, 2010 pp. 11.

* cited by examiner

REMOTE MANIPULATOR DEVICE

CROSS-REFERENCE TO RELATED APPLICATIONS

This application is a continuation-in-part of prior U.S. patent application Ser. No. 12/786,833, filed May 25, 2010, which claims priority to U.S. Provisional Patent Application No. 61/180,926 filed on May 25, 2009. The entire disclosures of the above applications are incorporated herein by reference.

BACKGROUND

This section provides background information related to the present disclosure which is not necessarily prior art.

This invention relates to automating the operation of medical devices.

Significant progress has been made in automating the navigation of medical devices in the body. Remote navigation systems, such as the Niobe® magnetic navigation system available from Stereotaxis, Inc., St. Louis, Mo., allows a physician to remotely orient the distal end of a medical device in the body. More recently, an automated advancer for advancing and retracting the device in the body has also become available, allowing more fully automated catheter navigation systems. However, a practical means of completely automating (under the supervision of a physician) the operation of medical devices, whereby a medical device can be automatically navigated to a particular location and then operated to perform some diagnostic or therapeutic procedure has not been available. This is particularly true with respect to automating the operation of conventional manually operated medical devices.

SUMMARY

This section provides a general summary of the disclosure, and is not a comprehensive disclosure of its full scope or all of its features.

Embodiments of the present invention provide a remote manipulator that not only can manipulate a conventional catheter, but can operate its controls. This not only allows the catheter to be remotely navigated, but also to be remotely operated. This allows a physician to conduct the procedure away from the patient, and also permits the complete automation of the procedure, with a computer navigating the catheter and operating the catheter without the need for human intervention.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
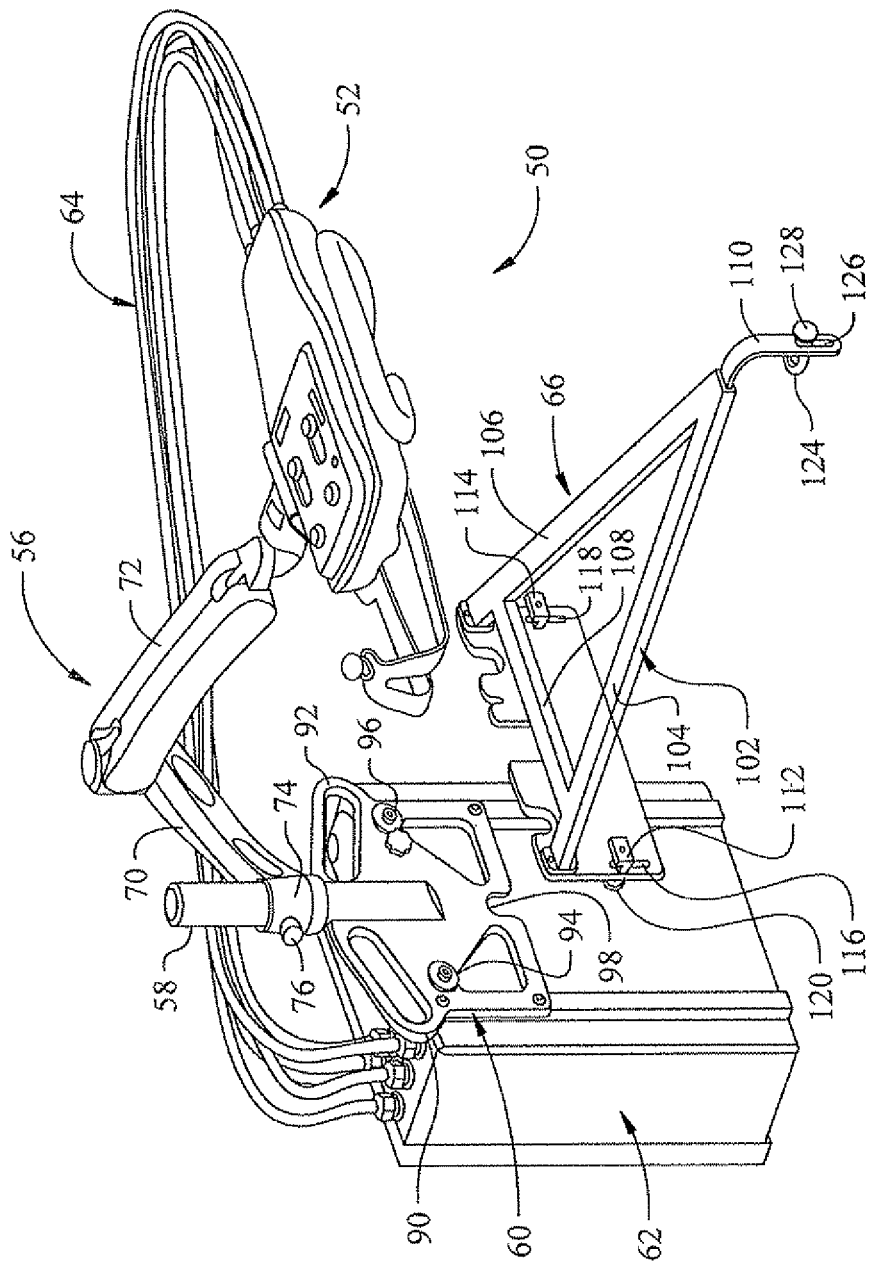
FIG. 1 is a front perspective view of a preferred embodiment of a remote manipulator device in accordance with the principles of this invention.
Figure 2:
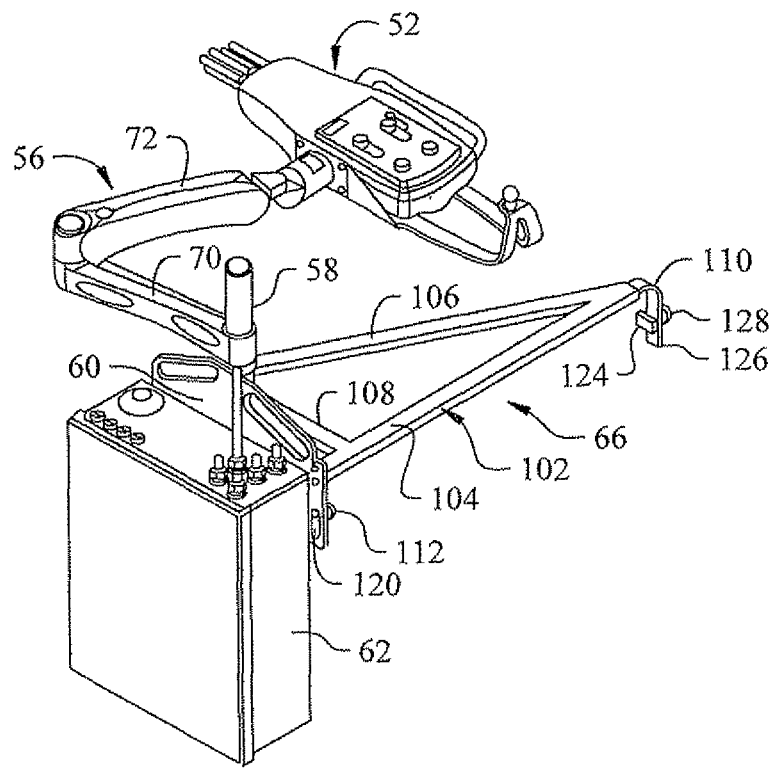
FIG. 2 is a rear perspective view of the preferred embodiment of the remote manipulator device, with the drive cables removed for clarity.
Figure 3:
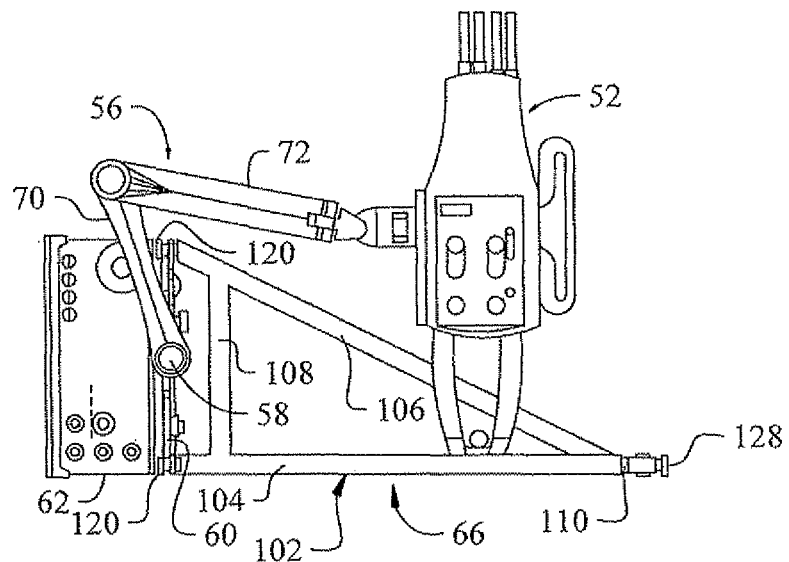
FIG. 3 is a top plan view of the preferred embodiment of the remote manipulator device, with the drive cables removed for clarity.
Figure 4:
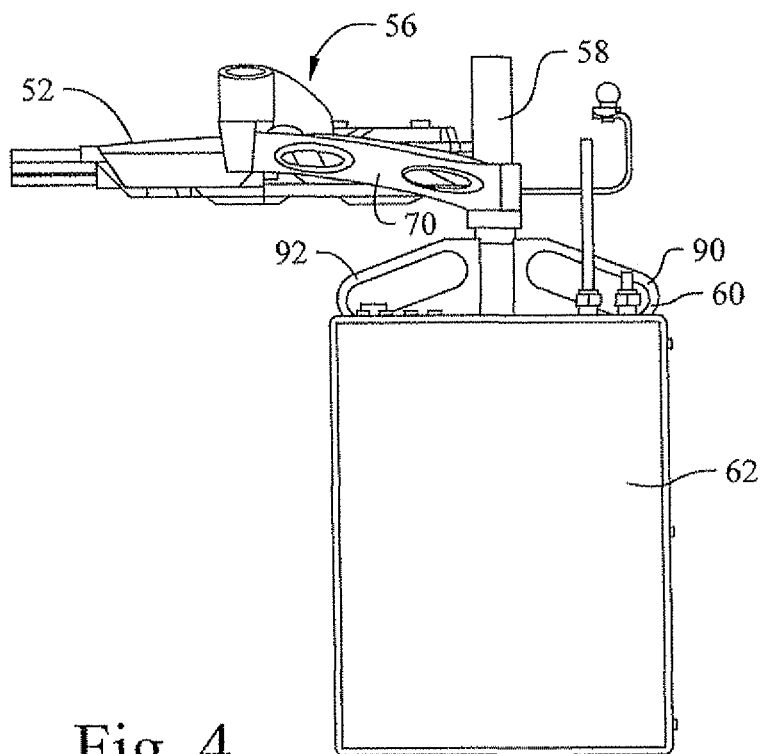
FIG. 4 is a rear elevation view of the preferred embodiment of the remote manipulator device, with the drive cables removed for clarity.
Figure 5:
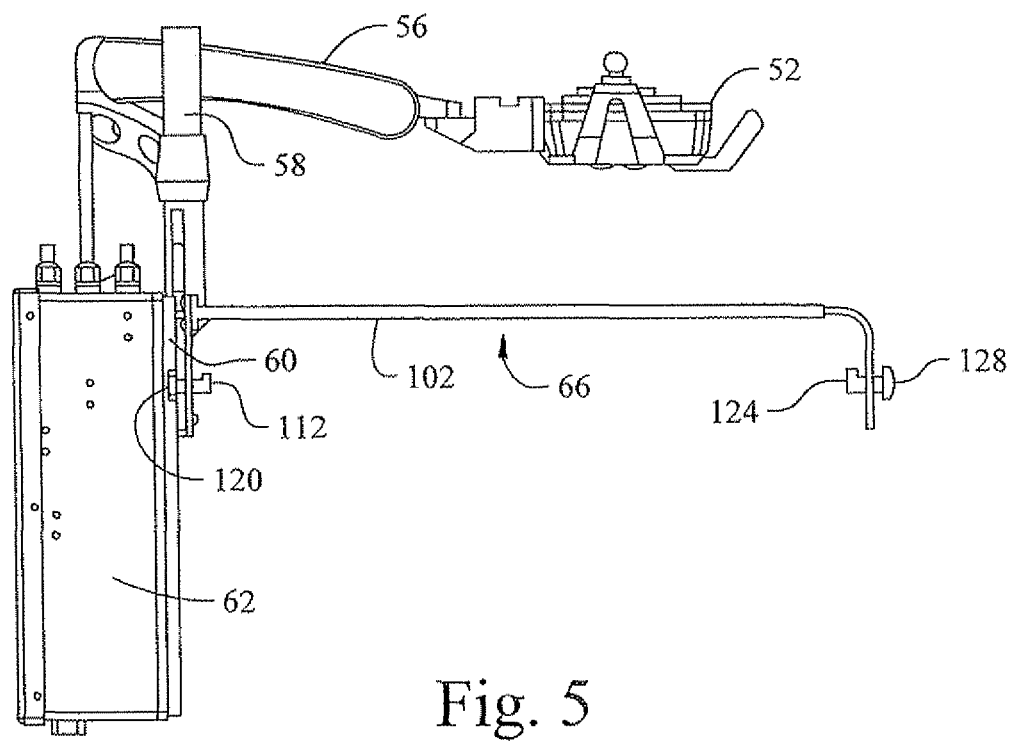
FIG. 5 is a left side elevation view of the preferred embodiment of the remote manipulator device, with the drive cables removed for clarity.
Figure 6:
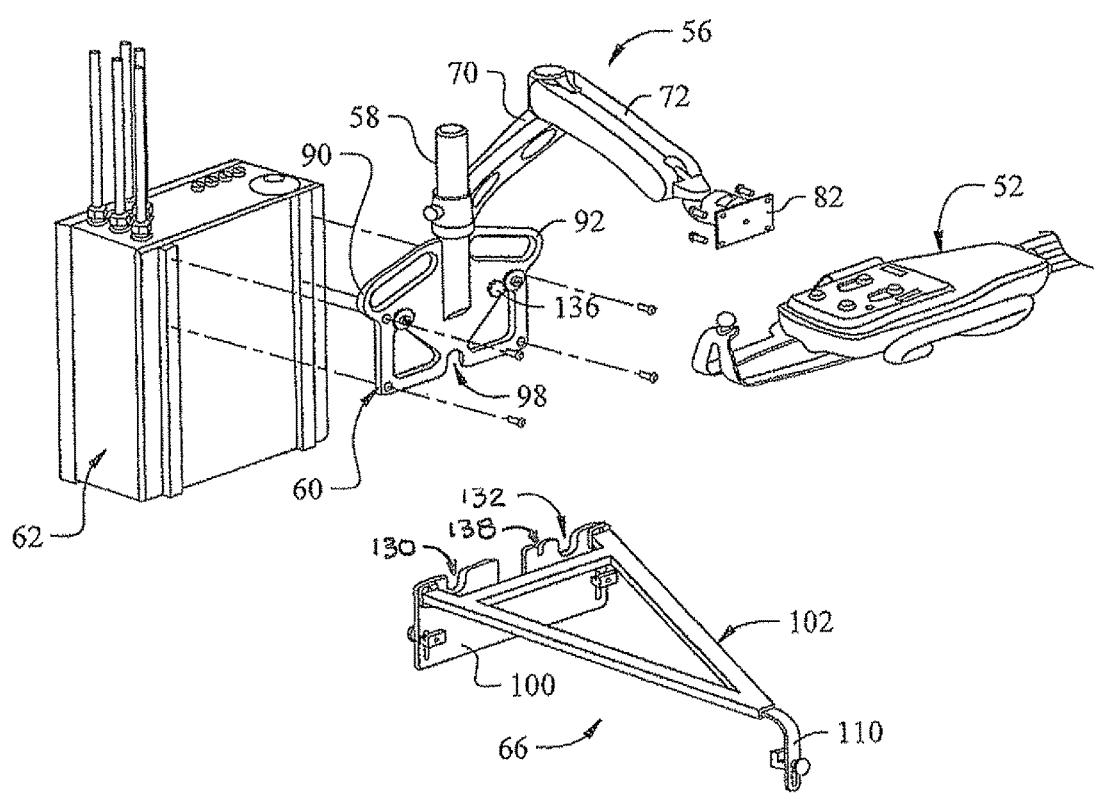
FIG. 6 is an exploded view of the preferred embodiment of the remote manipulator device.
Figure 7:
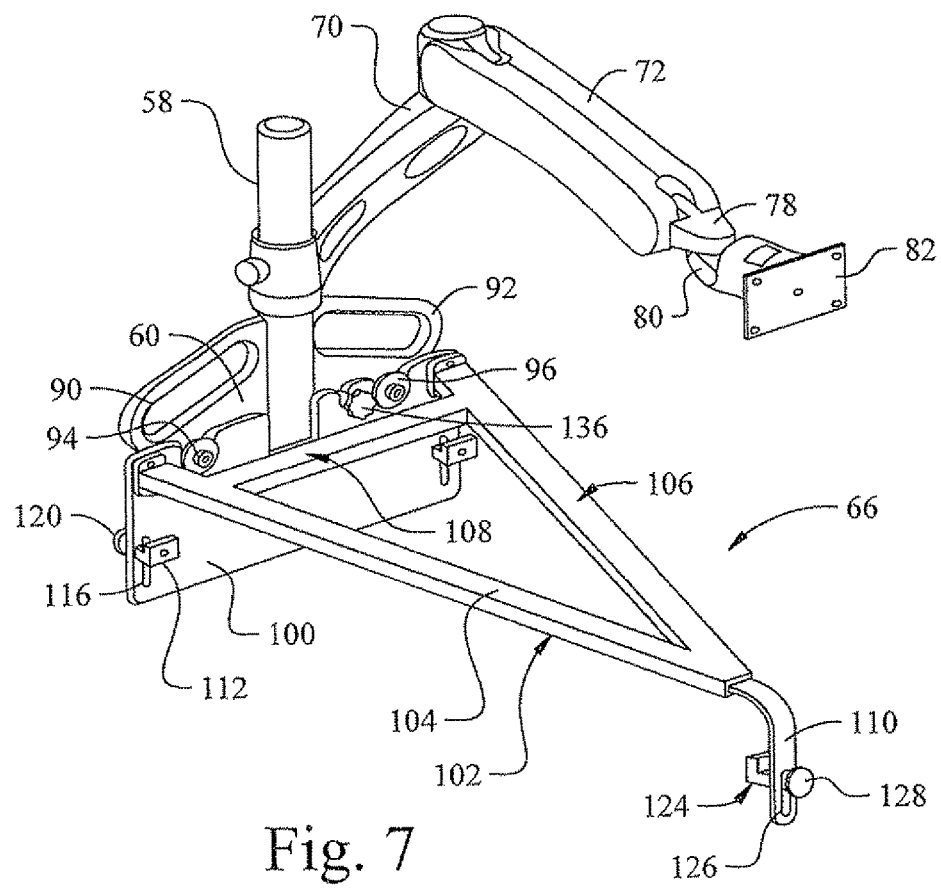
FIG. 7 is a front perspective view of the preferred embodiment of the remote manipulator device, with the device driver removed for clarity.
Figure 8:
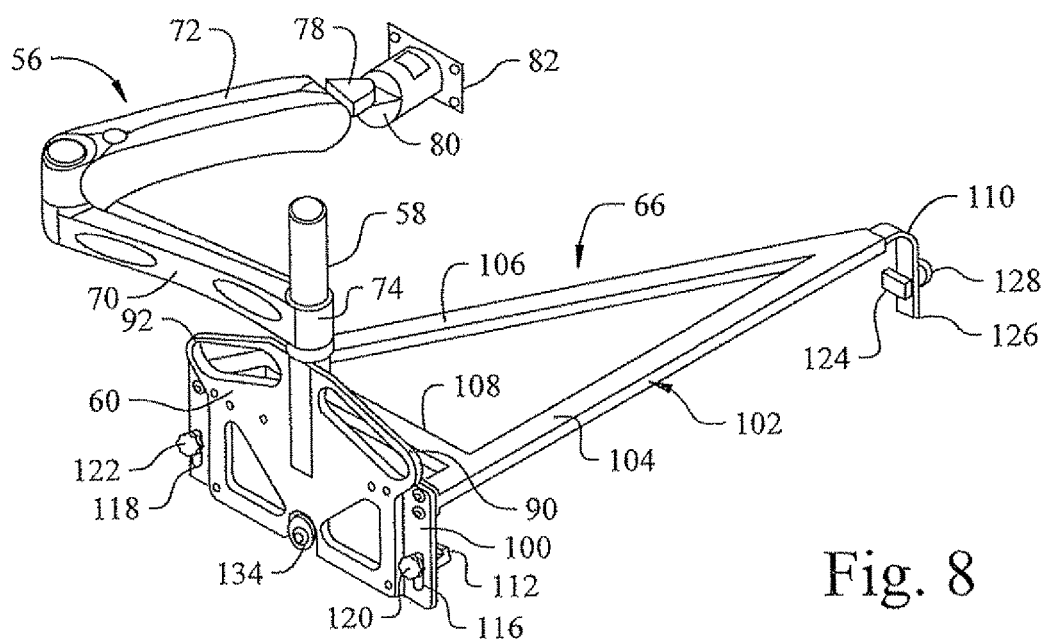
FIG. 8 is a rear perspective view of the preferred embodiment of the remote manipulator device, with the device driver removed for clarity.
Figure 9:
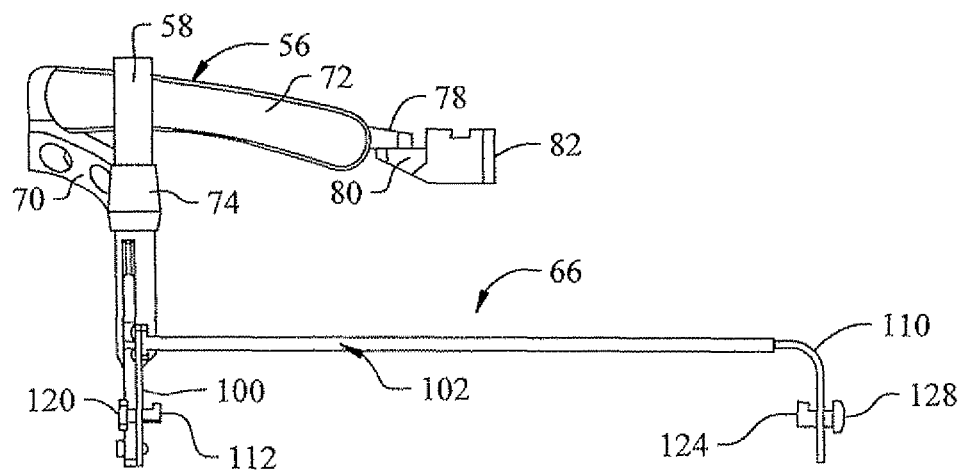
FIG. 9 is a left side elevation view of the preferred embodiment of the remote manipulator device, with the device driver removed for clarity.
Figure 10:
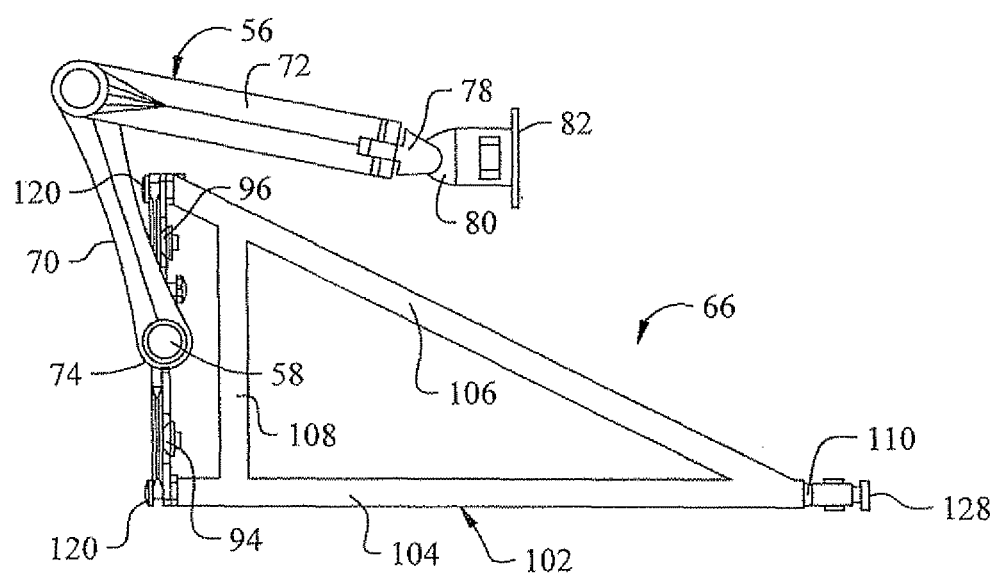
FIG. 10 is a top plan view of the preferred embodiment of the remote manipulator device, with the device driver removed for clarity.
Figure 11:
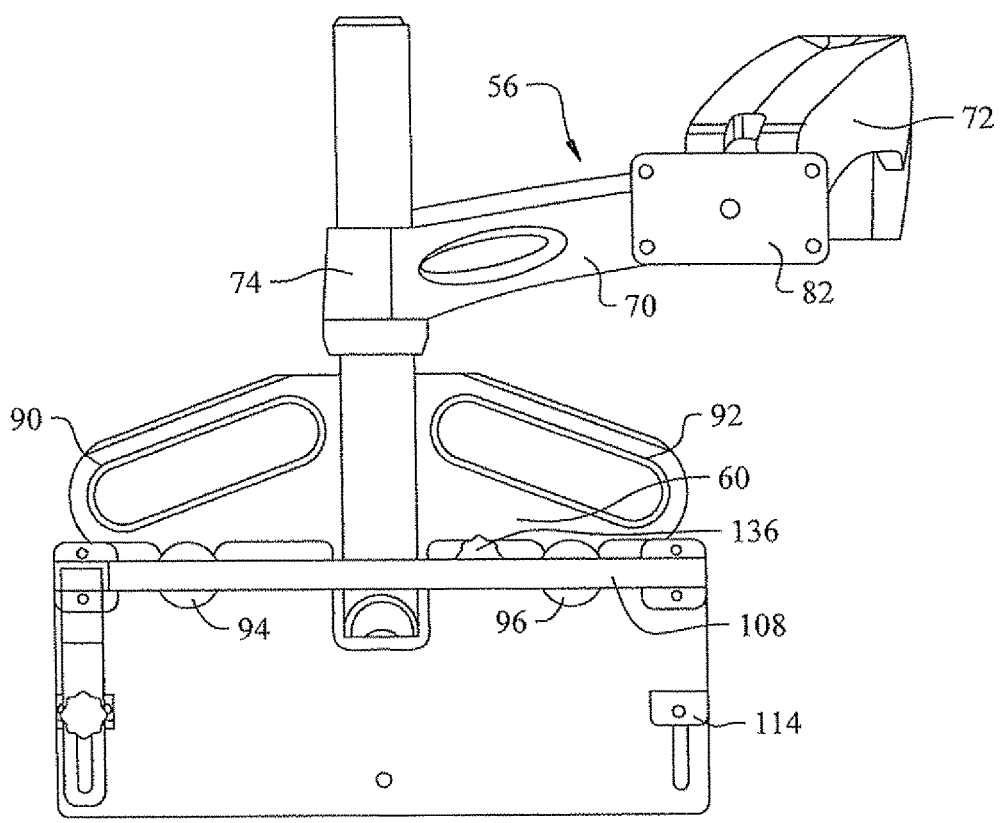
FIG. 11 is a front elevation view of the preferred embodiment of the remote manipulator device, with the device driver removed for clarity.

Example embodiments will now be described more fully with reference to the accompanying drawings.

A preferred embodiment of a remote manipulator device constructed according to the principles of this invention is indicated generally as 50 in FIGS. 1-5. The remote manipulator 50 is adapted to engage and operate a medical device. The medical device may be, for example, an electrophysiology catheter of the type comprising an elongate sheath having a handle at its proximal end, and an electrophysiology wire extending through the sheath and out the distal end, forming a loop. The handle preferably has controls for manipulating the distal end of the wire, for example a translatable control for bending the distal end, and a rotatable control for expanding and contracting the loop. While this preferred embodiment is described with respect to an electrophysiology catheter, this invention is not limited to electrophysiology catheters and applies to any medical device with an elongate portion, and a handle at the proximal end that can be manipulated to position and operate the distal end of the elongate portion of the medical device.

As shown in the FIGS. 1-5, the remote manipulator 50 comprises a device driver 52 for mounting and operating a device interface 54 (not shown in FIGS. 1-5), which in this preferred embodiment is both replaceable and disposable. The device driver 52 is mounted on the distal end of an articulated arm 56, whose proximal end is mounted on a post 58 on bracket 60. A controller 62, which can be mounted to the bracket 60, is connected to the device driver 52 by a plurality of flexible drive cables 64 to operate the device driver 52. A platform 66, attachable to the patient bed (not shown in FIGS. 1-5), can mount the bracket 60 and/or the controller 62.

As shown in FIG. 6-11, the articulated arm 56 comprises proximal and distal sections 70 and 72. Proximal section 70 has a collar 74 at its proximal end for mounting the proximal section 70 on the post 58. The proximal section 70 can translate up and down, and rotate around, the post 58. A locking screw 76 allows the collar and thus, the proximal section 70 to be releasably locked relative to the post 58. The distal end of the proximal section 70 is pivotally connected to the proximal end of the distal section 72. A lock (not shown) can be provided to releasably lock the proximal and distal sections 70 and 72 relative to each other. A first wrist element 78 is pivotally mounted to the distal end of the distal section 72 to pivot about a first axis generally perpendicular to the longitudinal axis of the distal section. A second wrist element 80 is pivotally mounted to the first wrist element to pivot about a second axis generally perpendicular to the first axis. A mounting plate 82 is rotatably mounted to the second wrist element 80 to rotate about a third axis, perpendicular to the first axis. The wrists pivoting about the first and second axis and the mounting plate rotating about the third axis are selectively releasably lockable, to releasably secure the articulated arm in a desired configuration with the device driver 52 in a desired location.

As also shown in FIGS. 6-11, the bracket 60 has hand loops 90 and 92 thereon. Pins 94 and 96 with enlarged conical heads project from the front face of the bracket 60. There is a semi-circular notch 98 in the bottom of the bracket 60.

As also shown in FIGS. 6-11, the platform 66 comprises a base plate 100, and a generally right-triangular frame 102, comprising legs 104 and 106, extending from the base plate 100 and leg 108 extending between the legs 104 and 106. A generally L-shaped bracket 110 telescopes from the leg 104 of the frame 102. Cleats 112 and 114 are mounted in slots 116 and 118 in the base plate 100 with threaded bolts 120 and 122 which have knurled heads that allow the cleats to be tightened against the side rail typically found on a patient bed. Similarly, a cleat 124 is mounted in slot 126 in the end of L-shaped bracket 110 with a threaded bolt 128 with a knurled head that allows the cleat to be tightened against the side rail of the patient bed. The top edge of the base plate 100 has semi-circular notches 130 and 132 for engaging the pins 94 and 96 on the bracket, and the back face of the base plate has a projecting pin 134 for engaging the semi-circular notch 98 in the bracket 60. A bolt 136 on the bracket 60 can be tightened to engage a slot 138 on the base plate 100 to secure the bracket and base plate 100.

Figure 12:
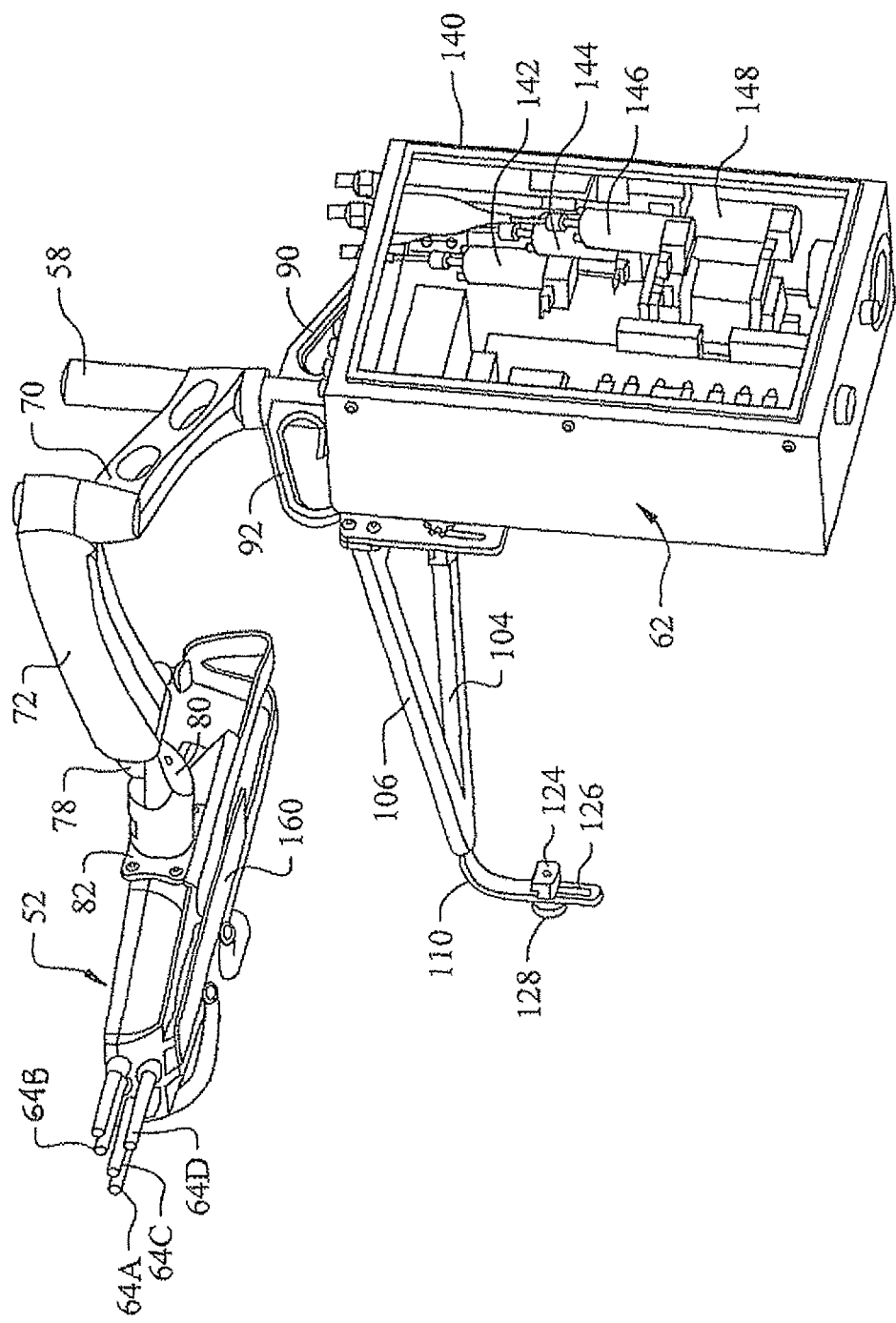
FIG. 12 is a rear perspective view of the preferred embodiment, with the cover removed from the controller.
Figure 13:
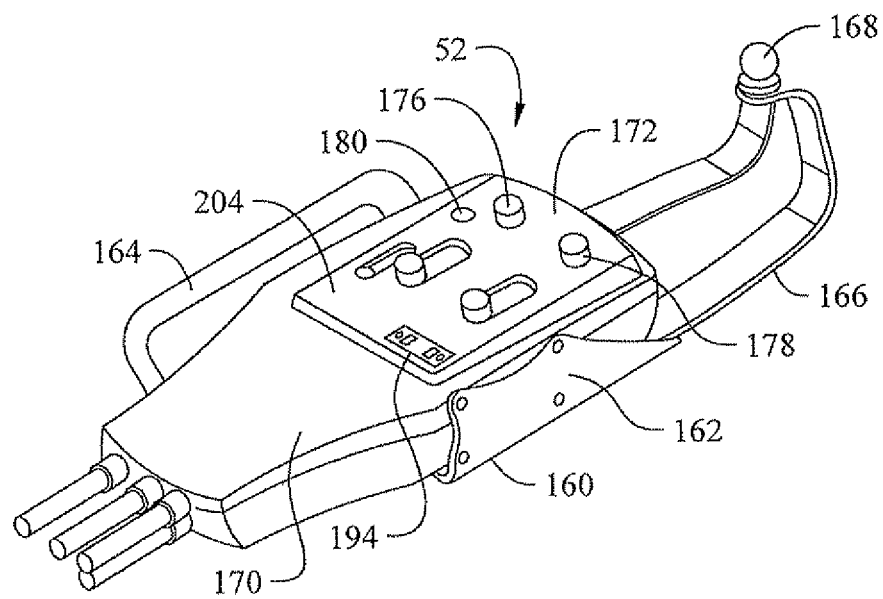
FIG. 13 is a perspective view of the device driver of the preferred embodiment.
Figure 14:
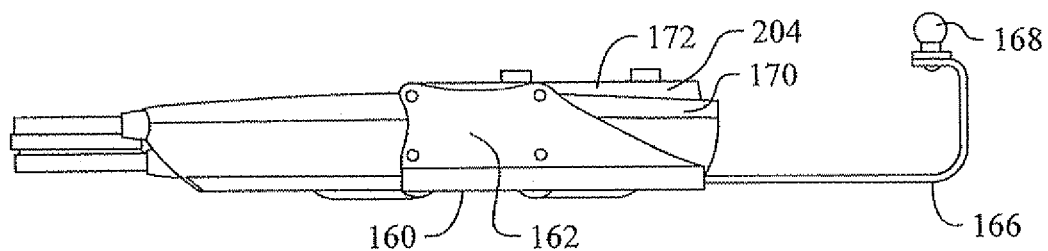
FIG. 14 is a side elevation view of the device driver of the preferred embodiment.
Figure 15:
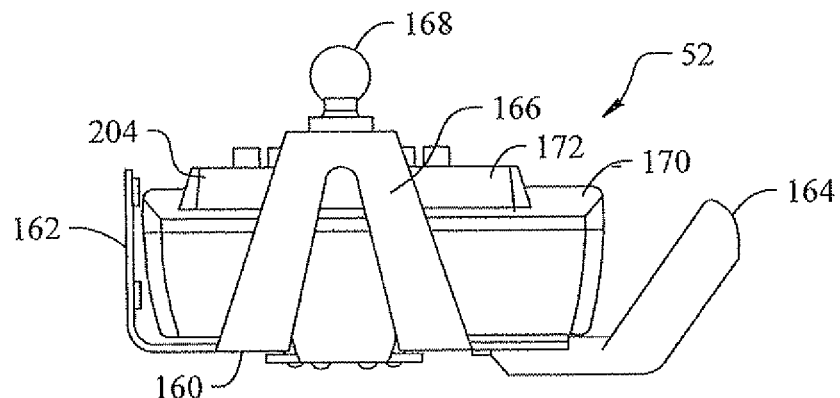
FIG. 15 is an front end elevation view of the device driver of the preferred embodiment.
Figure 16:
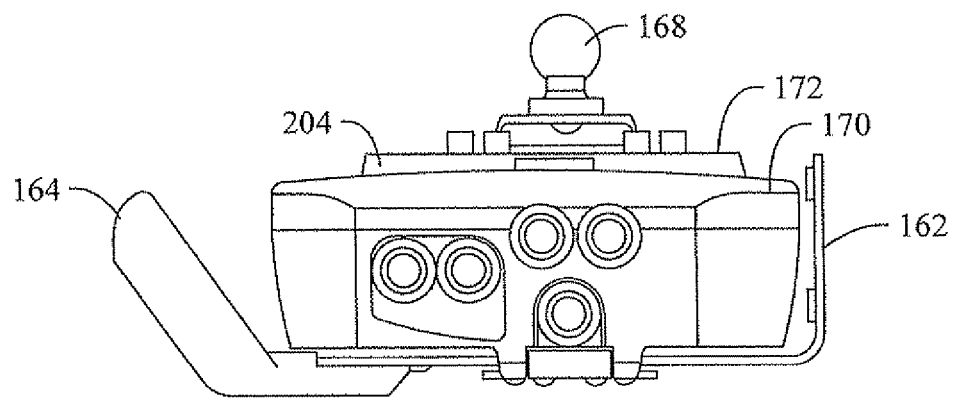
FIG. 16 is a rear end elevation view of the device driver of the preferred embodiment.
Figure 17:
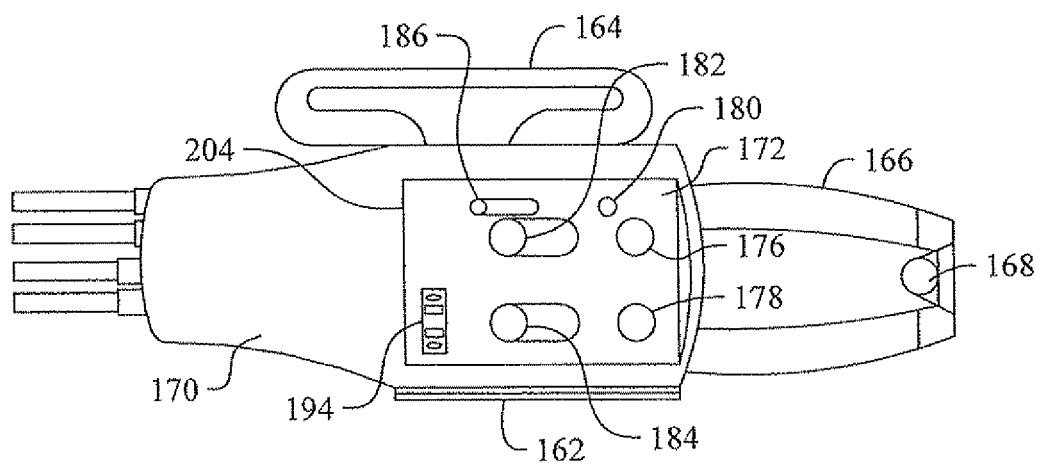
FIG. 17 is a top plan view of the device driver of the preferred embodiment.

The controller 62 can be attached to the bracket 60 and mounted on the platform 66. As shown in FIG. 12, the controller includes a housing 140 with four drives: a drive 142 for operating a first clamp driver on the device driver 52; a drive 144 for operating the second clamp translation driver on the device driver; a drive 146 for operating a second clamp driver on the device driver; and a drive 148 for operating the translation driver on the device driver for translating the device, as will be described in more detail below. Flexible drive cables 64 connect each drive in the controller with its respective driver in the device drive 52.

As shown in FIGS. 13-21, the device driver 52 comprises a base 160 having a mount 162 for attaching the device driver to the mounting plate 82 on the end of the articulated arm 56. A hand loop 164 on the opposite side of the base 160 from the mount 162 can be provided for gripping the device driver 52 to reposition it. A generally V-shaped bracket 166 projects from the front of the base 160, the end of the bracket is bent upwardly and has a fixture 168 mounted thereon for mounting a sheath, as described in more detail below. The device driver 52 further comprises a body 170 mounted on the base 160 to translate forwardly and rearwardly with respect to the base.

The top surface of the body 170 has a platform 172 for mounting a device interface 54 thereon. As described below, the device interface 54 has one or more clamps 174 (not shown in FIGS. 13-21) for engaging and operating the handle of an elongate medical device. The platform 172 has a first pair of mounting sockets 176 and 178 for engaging a clamp 174 on the device interface 54, and a drive socket 180 for receiving and engaging a drive shaft of the clamp to operate the clamp. In this preferred embodiment, the platform 172 also has a second pair of mounting sockets 182 and 184 for engaging a second clamp 174 on the device interface 54, and a drive socket 186 for receiving and engaging a drive shaft of the second clamp to operate the second clamp. The second pair of sockets 182 and 184, and the drive socket 186 are disposed in slots so that they can translate relative to the first set of sockets 176 and 178, to accommodate relative movement between the clamps 174 on the device interface 54, as will be described in more detail below. There is an electrical contact pad 194 on the platform 172 for making electrical contact with a corresponding electrical contact pad 196 on the device interface 54.

Figure 18:
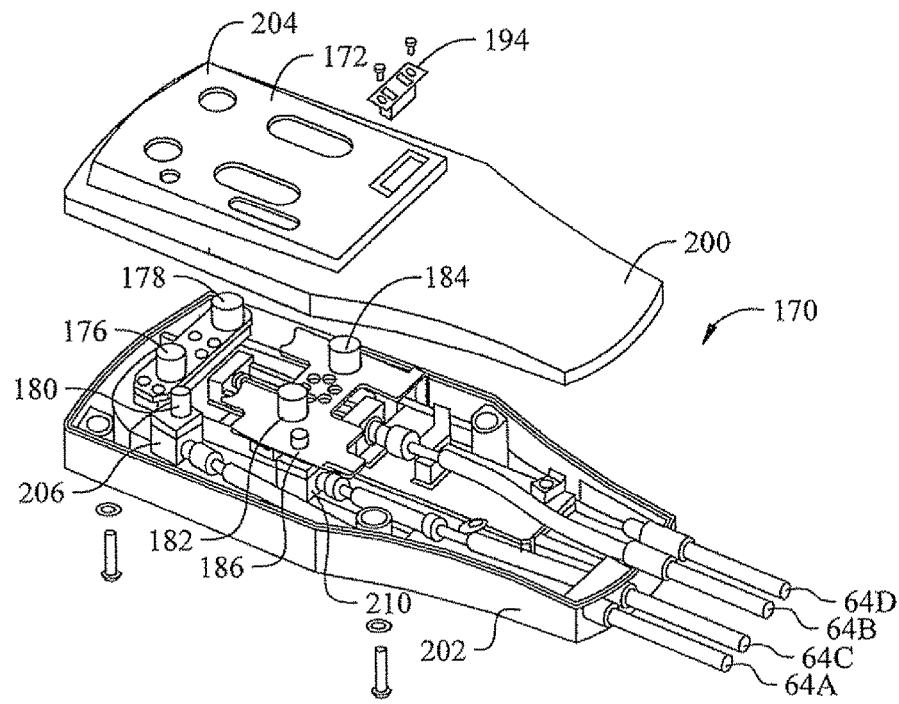
FIG. 18 is a perspective view of the body of the device driver, with the upper and lower members separated to show the details of construction.
Figure 19:
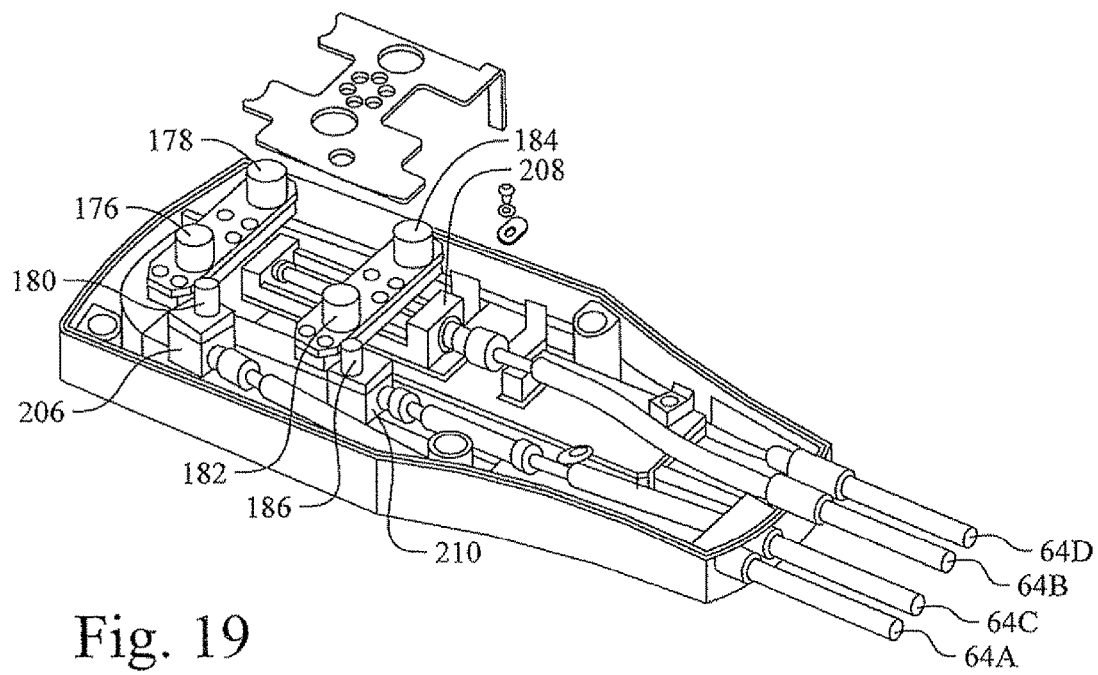
FIG. 19 is a perspective view of the body of the device driver, with the upper member removed to show the details of construction.
Figure 20:
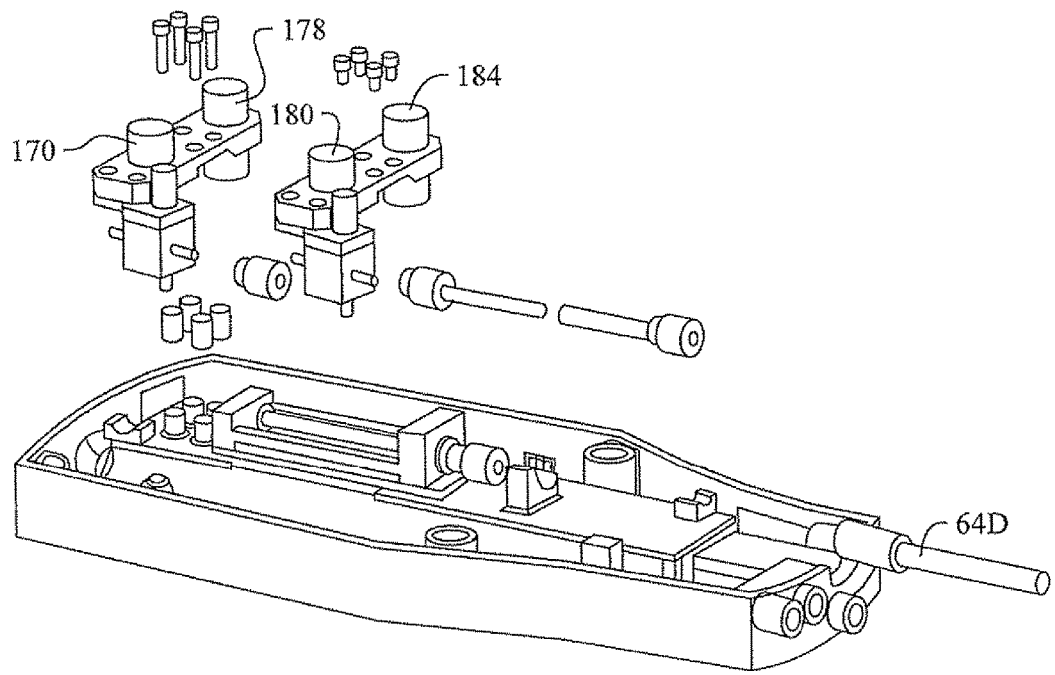
FIG. 20 is an exploded perspective view of the body of the device driver, with the upper member removed.
Figure 21:
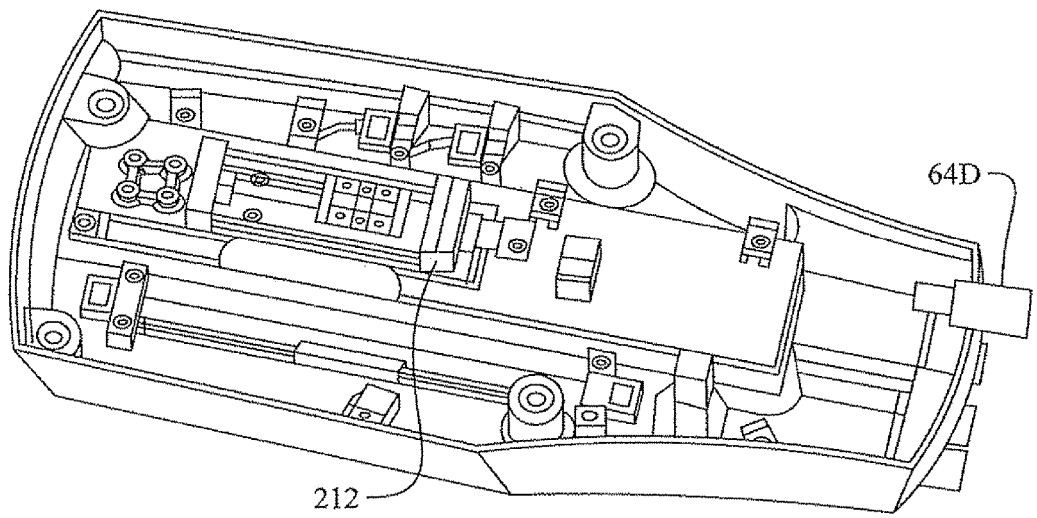
FIG. 21 is an exploded perspective view of the body of the device driver, with parts removed to show details of construction.
Figure 22:
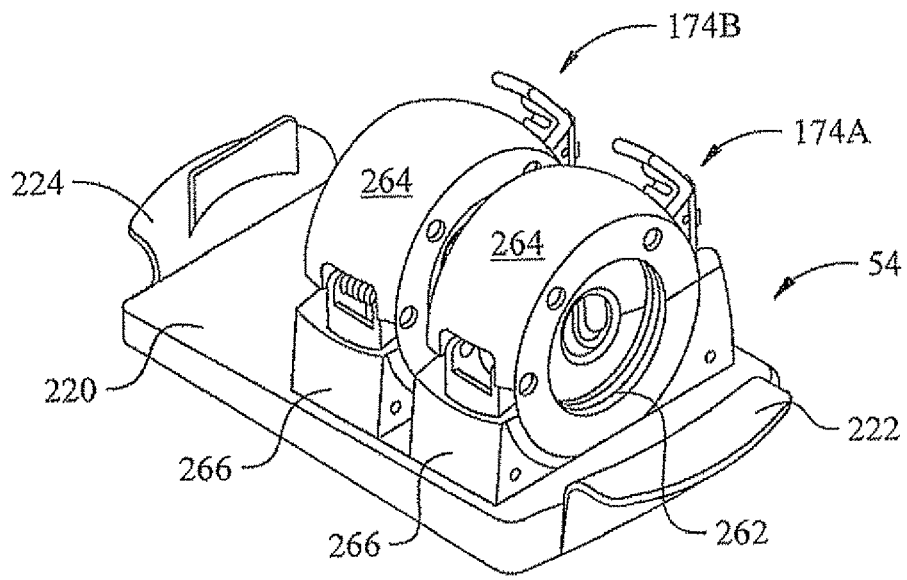
FIG. 22 is a perspective view of the device interface of the preferred embodiment.
Figure 26:
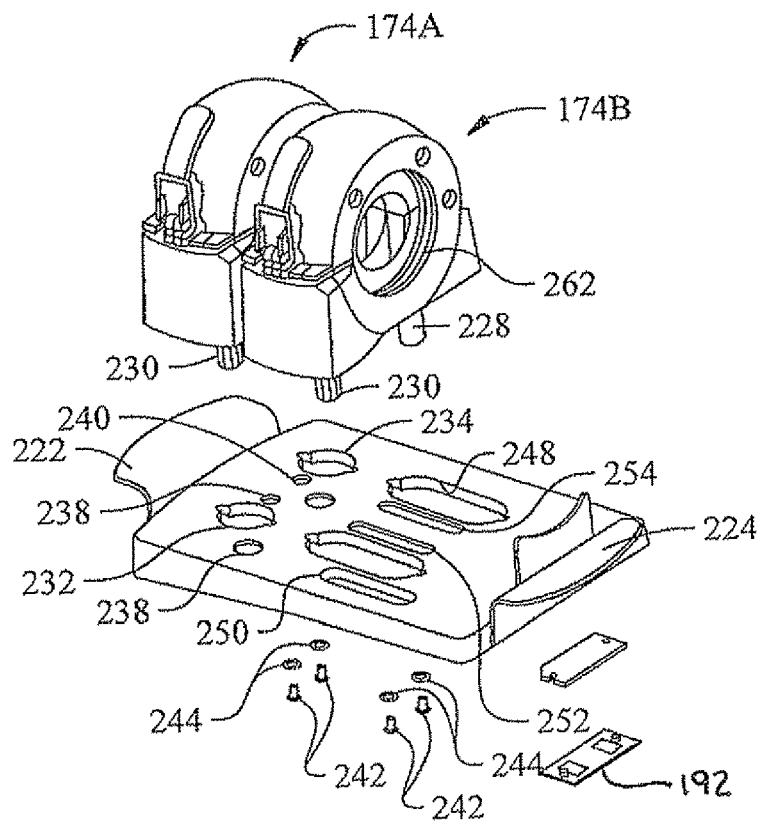
FIG. 26 is an exploded perspective view of the device interface of the preferred embodiment.
Figure 23:
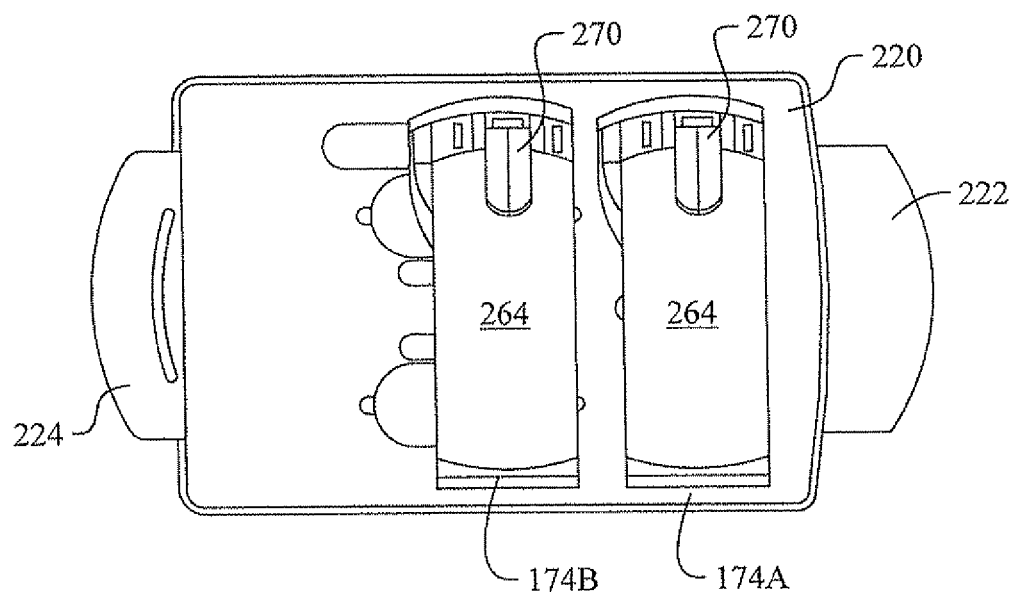
FIG. 23 is a top plan view of the device interface of the preferred embodiment.
Figure 24:
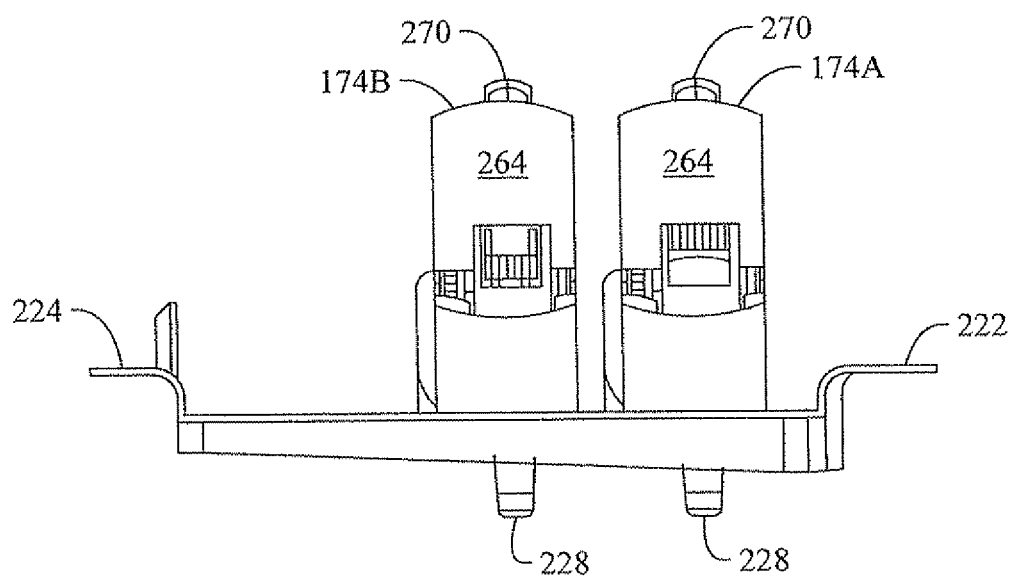
FIG. 24 is a side elevation view of the device interface of the preferred embodiment.
Figure 25:
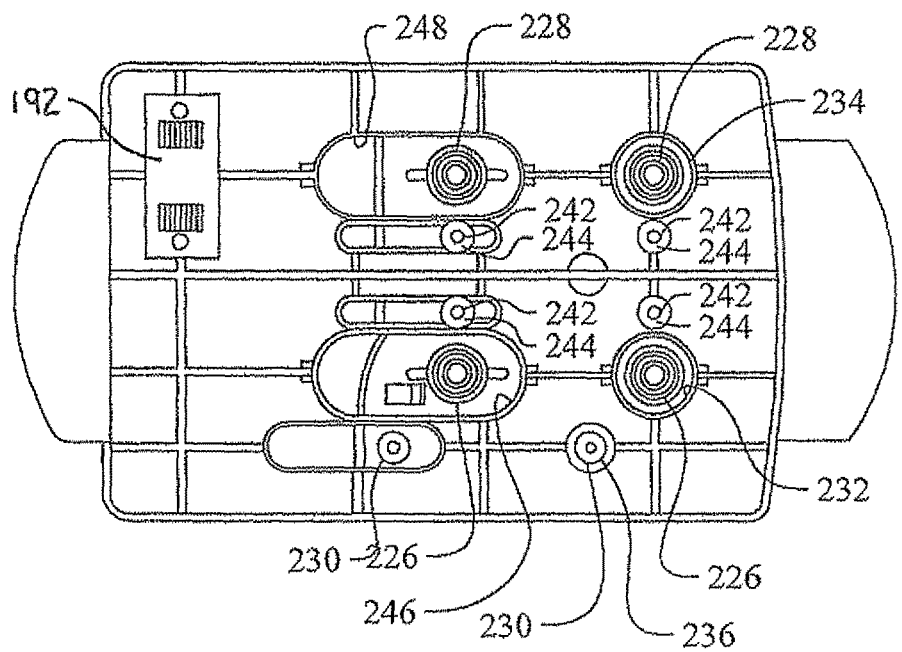
FIG. 25 is a bottom plan view of the device interface of the preferred embodiment.
Figure 27:
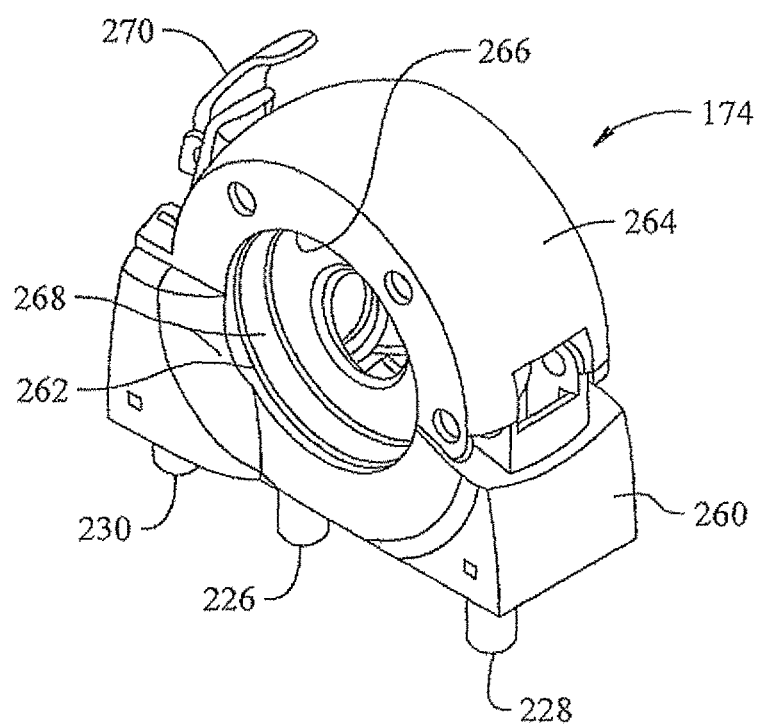
FIG. 27 is a perspective view of one of the clamps used in the device interface of the preferred embodiment.
Figure 28:
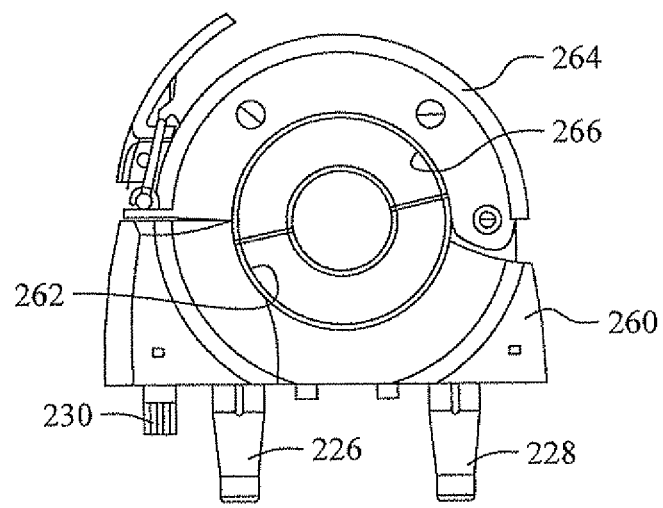
FIG. 28 is a rear elevation view of the clamp.
Figure 29:
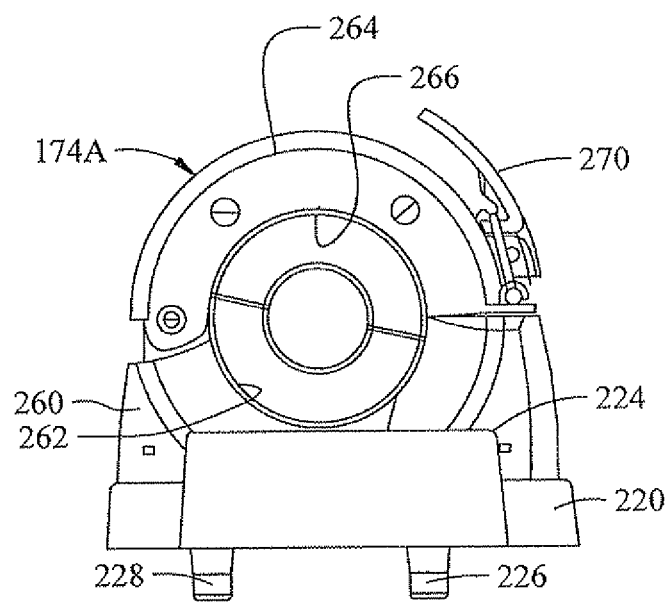
FIG. 29 is a front elevation view of the clamp.
Figure 30:
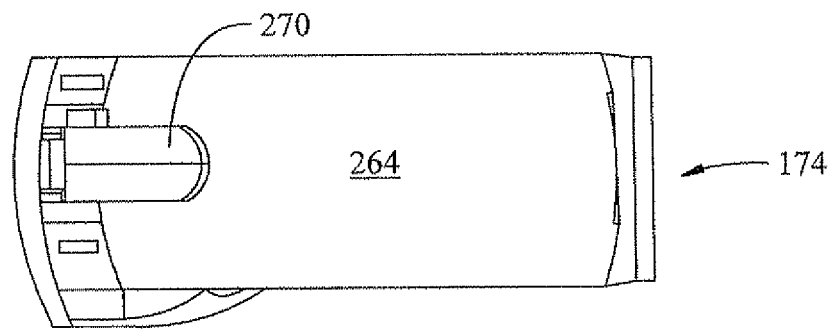
FIG. 30 is a top plan view of the clamp.
Figure 31:
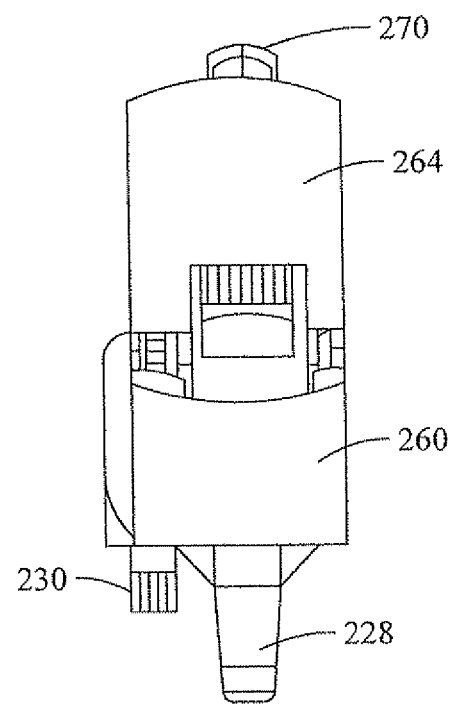
FIG. 31 is a side elevation view of the clamp, showing the hinged connection between the base and cover.

As shown in detail in FIG. 18, the body 170 comprises upper and lower housing members 200 and 202. The platform 172 is formed in the top of the upper housing member 200, and comprises a raised platform area 204 with openings for the sockets 176 and 178 and 182 and 184, as well as contact pad 194. As shown in FIG. 19, in the lower housing member 202, the distal end of flexible drive cable 64A, connects the drive 142 to a transmission 206 for turning socket 180 to operate a first clamp 174 on a device interface 54 seated on the platform 172. The distal end of a cable 64B connects the drive 144 to a screw-driven translation mechanism 208 for translating the second pair of sockets 182 and 184 relative to first pair or sockets 176 and 178. The distal end of cable 64C connects the drive 146 to a transmission 210 for turning socket 186 to operate a second clamp 174 on a device interface 54. Lastly, a flexible drive cable 64D connects the drive 148 to a screw translation mechanism 212 (FIG. 21) for moving the body 170 relative to the base 160.

As shown in FIGS. 22-26, the device interface 54 comprises a tray 220 that is adapted to fit onto the raised platform 204 forming the platform 172 on the device driver 52. The tray 220 has a generally rectangular shape, but preferably has a curved side or other feature that prevents the tray from being installed on the device driver 52 incorrectly. There are handles 222 and 224 at either end of the tray 220 to facilitate handling the tray. One or more clamps 174 are mounted on the tray 220. In this preferred embodiment there are two clamps, a first clamp 174A, which is fixedly mounted with respect to the tray 220, and a second clamp 174B, which is slidably mounted with respect to the tray 220. As described in more detail below, each of the clamps has two depending pins 226 and 228, and a depending drive spline 230. The tray 220 has a pair of holes 232 and 234 for receiving the pins 226 and 228 of clamp 174A, and a hole 236 for receiving the drive spline 230. Two mounting holes 238 and 240 allow the clamp 174A to be secured to the tray with screws 242 and washers 244. The tray 220 also has a pair of slots 246 and 248 for receiving the pins 226 and 228 of clamp 174B, and a slot 250 for receiving the drive spline 230. Two mounding slots 252 and 254 allow the clamp 174B to be secured to the tray with screws 242 and washers 244. The slots 246, 248, 250 and 252 and 254 allow the clamp to translate on the tray 220. A contact plate 192 is secured on the bottom of the tray for making electrical contact with the contact pad 194 on the device driver 52.

As shown in FIGS. 27-36, each of the clamps 174 comprises a base 260 which carries the pins 226 and 228 and the drive spline 230. The base 260 has a semi-circular notch 262. A generally arcuate cover 264 has a semi-circular notch 266 therein which is hingedly attached at one end to the base 260, to pivot between an open position and closed position, in which the semi-circular notch 262 in the base 260 and the semi-circular notch 266 in the cover 264 form a generally circular opening 268 through the clamp. An over-center latch 270 releasably secures the other end of the cover 264 to the base 260 to retain the cover in its closed configuration.

Figure 32:
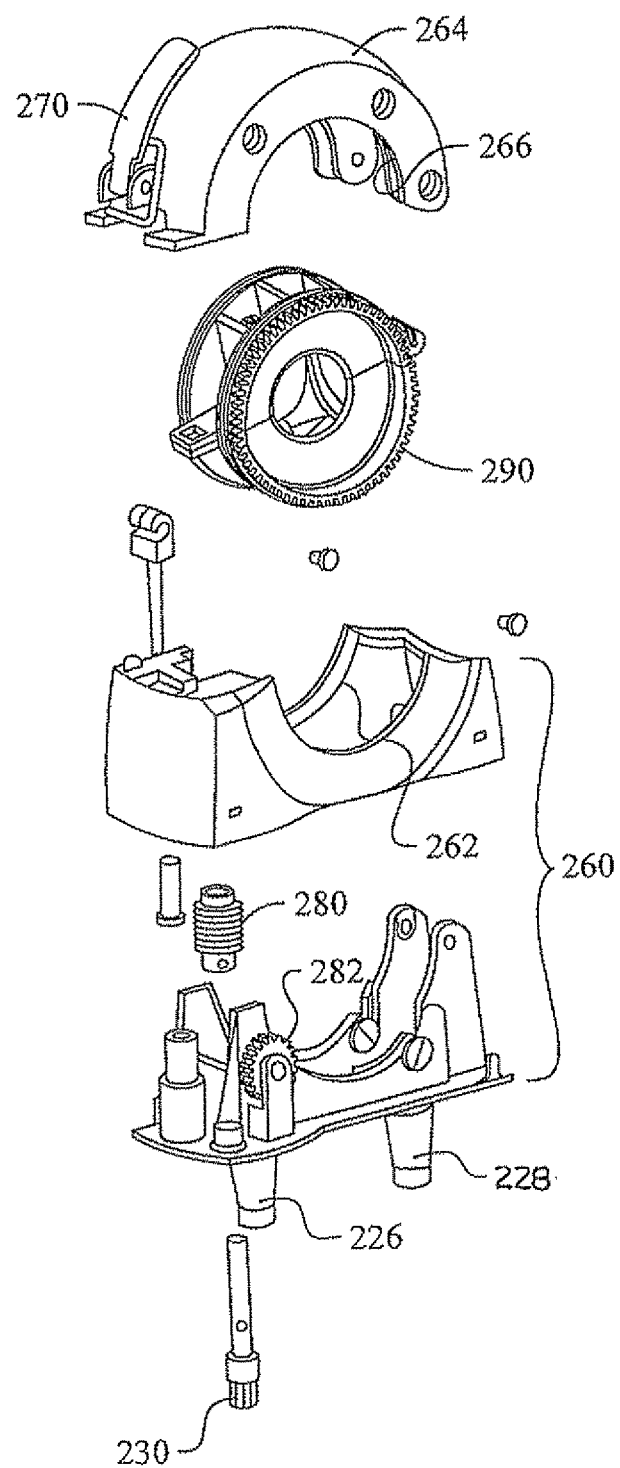
FIG. 32 is an exploded perspective view of the clamp.
Figure 34:
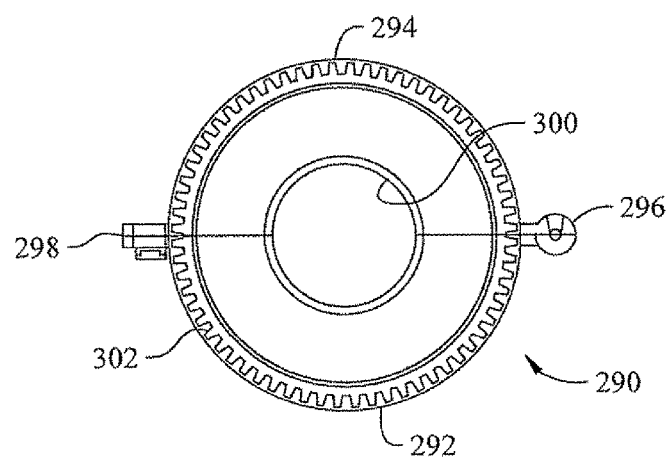
FIG. 34 is a front elevation view of the split ring adapter.
Figures 33, 35:
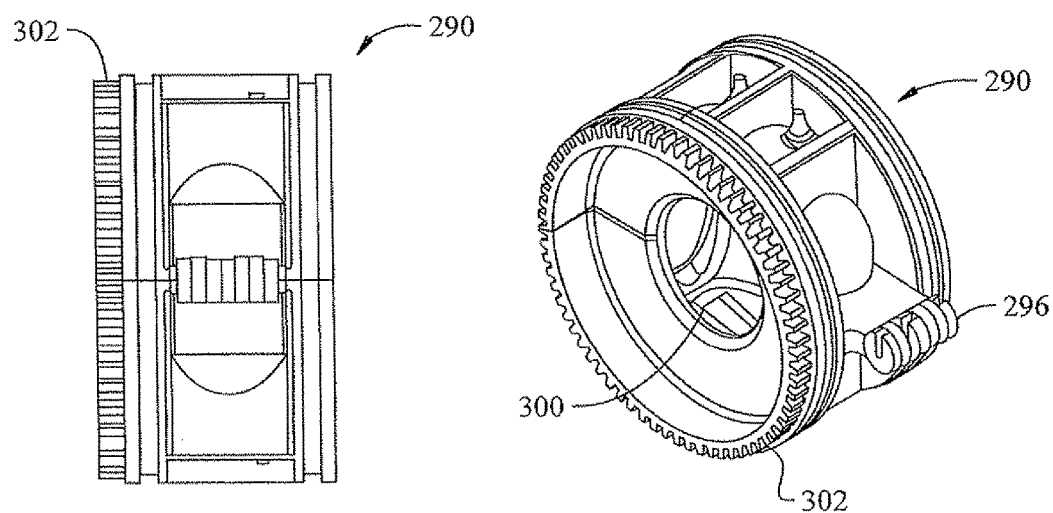
FIG. 33 is a perspective view of the split ring adapter used in the clamp.
FIG. 35 is a side elevation view of the split ring adapter.
Figure 36:
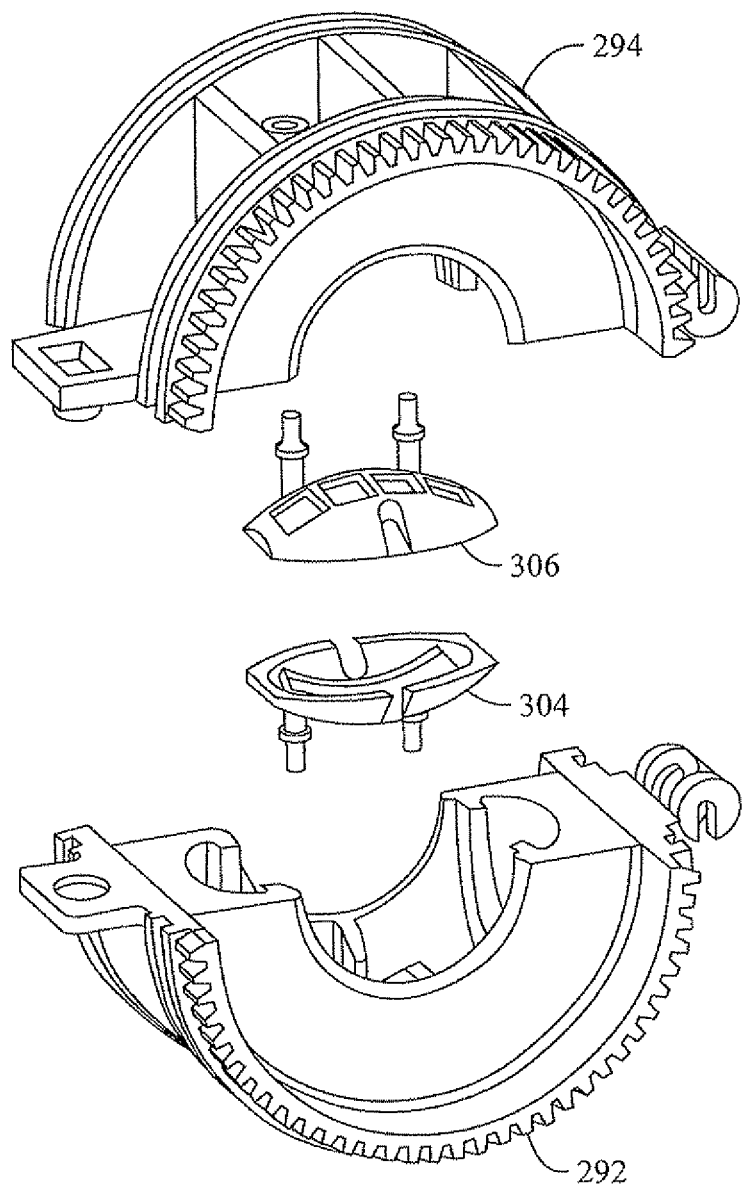
FIG. 36 is an exploded perspective view of the split ring adapter.

As best shown in FIG. 32, a worm gear 280 is mounted on the end of the spline 230 to rotate with the spline. The worm gear engages a sprocket 282, so that the sprocket turns when the spline 230 turns.

A split adapter ring 290 comprises first and second generally semi-circular halves 292 and 294, and has a hinged connection 296 at one side to pivot between an open position and a closed position in which the halves 292 and 294 form a ring. The other ends of the halves 292 and 294 are releasably connected, for example with a snap latch 298 to form a ring with a central opening 300. The split adapter ring 290 can be secured around a portion of the handle of a conventional manually operated medical device. The split adapter ring 290 has an associated ring gear 302 and is adapted to fit inside the clamp 174B, with the ring gear 302 engaged with the sprocket 282. The interior of each of the halves 292 and 294 can be specially adapted to receive the handle of a particular medical device, or various inserts (for example inserts 304 and 306 shown in FIG. 36) can be used to adapt a standardized halves to accommodate different medical devices.

Figure 41:
FIG. 41 is a perspective view of an alternative arrangement of the preferred embodiment of the remote manipulator device, adapted for rotating a sheath and advancing a medical device through the rotating sheath.
Figure 42:
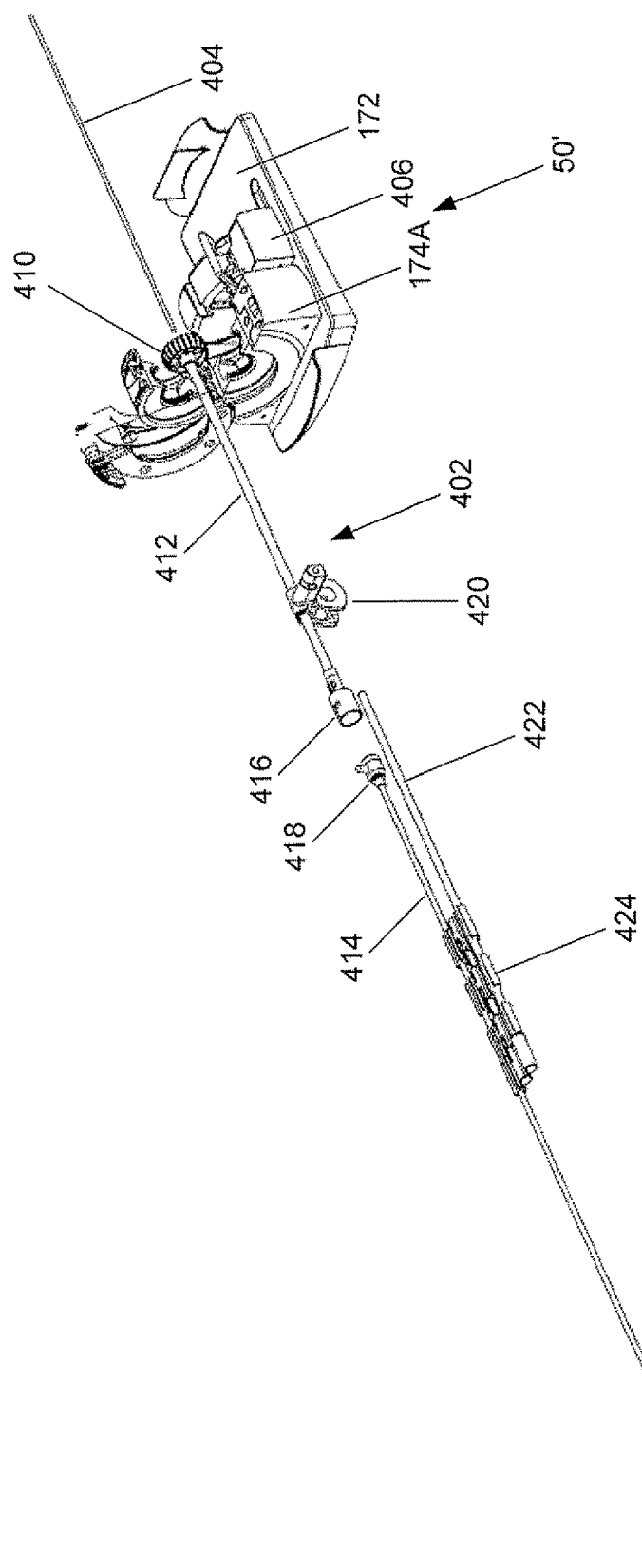
FIG. 42 is a perspective view of the alternative arrangement of FIG. 41, with the clamp open to show engagement with the sheath.
Figure 43:
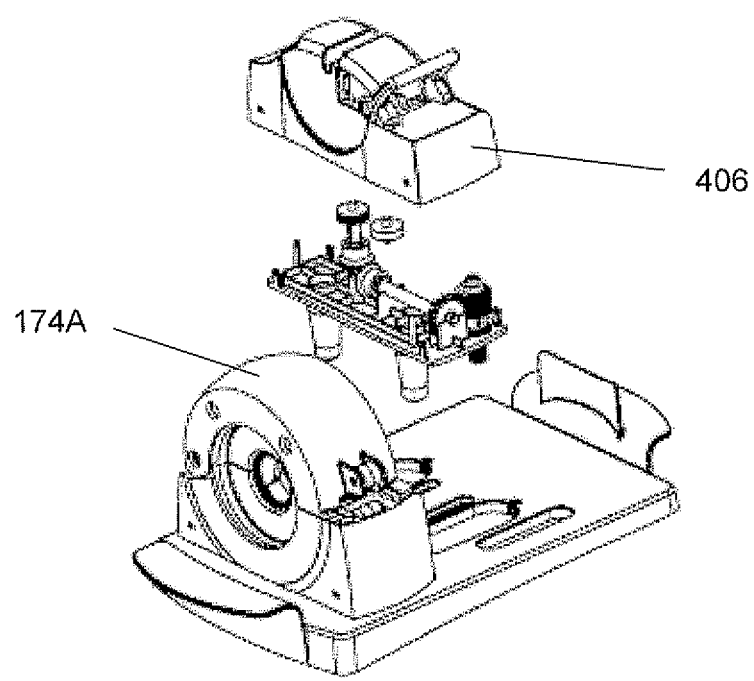
FIG. 43 is a perspective view of the rotating and advancing mechanism of the alternative arrangement of the preferred embodiment shown in FIG. 41.

An alternative arrangement of the preferred embodiment of the remote manipulator device indicated as 50' is shown in FIGS. 41-43. The remote manipulator 50' is similar in construction and arrangement to the remote manipulator 50, and corresponding parts are identified with corresponding reference numerals. However instead engaging the handle at the proximal end of a medical device, the remote manipulator 50' is adapted to engage and rotate sheath 402, and engage and advance and retract elongate flexible medical device 404 in the lumen of the sheath In particular with remote manipulator 50', the clamp 174A of remote manipulator 50 is adapted to engage and rotate a sheath 402 surrounding the proximal portion of the medical device 404. The clamp 174B of remote manipulator 50 has been replaced with a device advancer 406 that engages and advances the proximal portion of the medical device 404 extending from the proximal end of the sheath 402. Thus the clamp 174B can rotate the sheath 402, whose distal end may have a shaped configuration, such as a bend or twist, in order to orient the distal end the medical device 404 as it exits the distal end of the sheath. The device advancer 406 engages the proximal end of the medical device and can advance and retract the medical device through the lumen of the sheath 402.

The device advancer 406 may similar in construction to the device advancer 30 disclosed in U.S. Pat. No. 7,635,342, incorporated herein by reference. Like the device 30 of U.S. Pat. No. 7,632,342, the device advancer 406 is preferably top-loading, allowing the medical device 404 to be introduced into and removed from the advancer at any point intermediate its proximal and distal ends. However, unlike device advancer 30 of U.S. Pat. No. 7,632,342, the device advancer 406 is adapted to mount on the platform 172 and engage and be driven by the device driver 52. As shown in FIG. 43, the advancer has a base particularly adapted to mount on, and be driven by, the platform 172.

The medical device 404 may have a handle at its proximal end that can be manually manipulated to operate the device. The remote manipulator 50' operating to rotate the sheath 402 and to advance and retract the medical device 404 through the lumen of the sheath 402, and the device 404 otherwise being manually operated via its handle. However in order to fully enable remote operation it may be desirable to operate remote manipulator 50' and a remote manipulator 50 that engages the handle of the medical device and can operate it remotely as well.

As shown in FIG. 42, the proximal end of the sheath 402 can have a knurled end 410, or other configuration to ensure that it can be engaged within the clamp 174A and rotated. In the preferred embodiment the sheath 402 comprises a relatively rigid proximal section 412 connected to the knurled end 410, and a relatively more flexible distal section 414, which can be connected to the proximal section with mating connector elements 416 and 418. The distal end of the distal section 414 can have a bend, twist or other configuration to help orient the distal end of medical device 404 as it exits the distal end of the sheath 402. As shown in FIG. 42 an clamp 420 can engage the proximal section of the sheath, and support a rod 422, that in turn supports a bracket 424 that supports the proximal portion of the distal section 414, to reduce undesired bending and flexing of the sheath.

Figure 44:
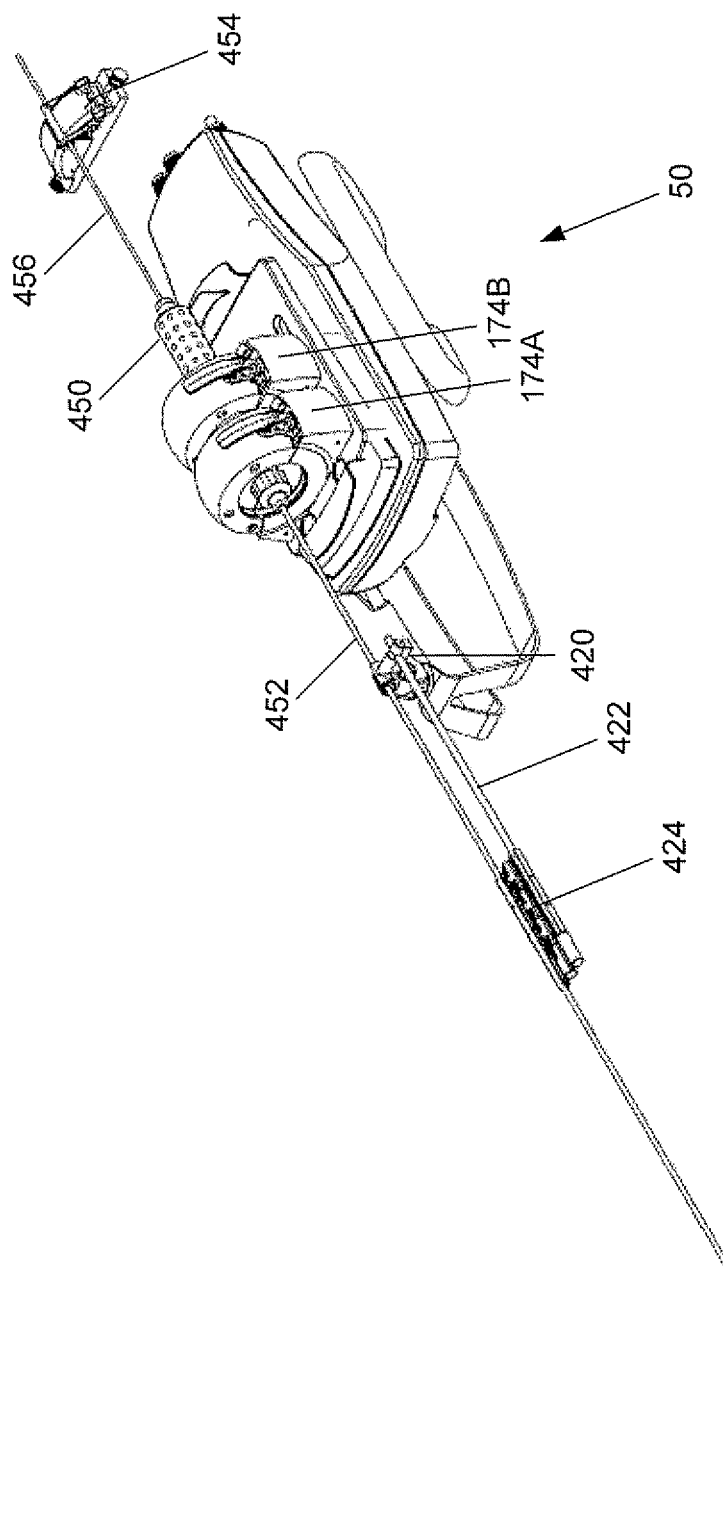
FIG. 44 is a perspective view of an alternate arrangement of the remote manipulator of the preferred embodiment for rotating, operating and advancing a manipulable sheath, and for advancing and retracting an elongate medical device in the lumen of the manipulable sheath.

Another alternate arrangement of the remote manipulator of the preferred embodiment is shown in FIG. 44 as it would be arranged for rotating, operating and advancing a manipulable sheath and for advancing and retracting an elongate medical device in the lumen of the manipulable sheath. The remote manipulator 50 engages the handle 450 of a remotely manipulable sheath 452. The remote manipulator 50 can rotate, advance and retract the sheath 452 and operate the controls on the handle 450 to cause the distal end of the sheath to bend or turn. A separate advancer 454 can be provided to advance and retract a medical device 456 through the lumen of the sheath 452. Thus the manipulable sheath 452 can be rotated, advanced and retracted, and operated, and a medical device can be advanced and retracted through the lumen of the manipulable sheath, remotely.

Figure 45:
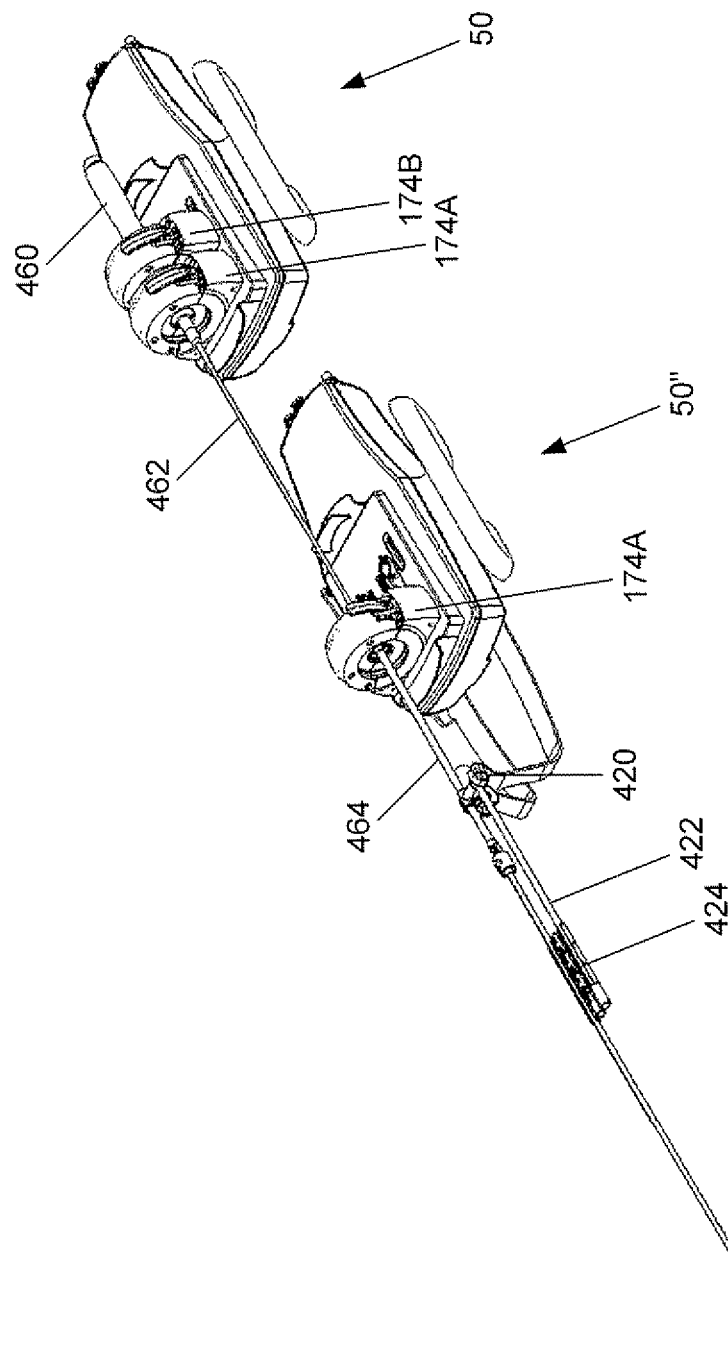
FIG. 45 is a perspective view of an alternate arrangement of the remote manipulator of the preferred embodiment for rotating and advancing a sheath and for operating and advancing an elongate medical device in the lumen of the sheath.

Another alternate arrangement of the remote manipulator of the preferred embodiment is shown in FIG. 45 as it would be arranged for rotating and advancing a sheath and for operating and advancing and retracting a medical device in the lumen of the sheath. The remote manipulator 50 engages the handle 460 on the proximal end of a remotely manipulable medical device 462. The remote manipulator 50 can advance retract the medical device, and operate the controls on the handle 460 to cause the distal end of the medical device 462 to bend or other otherwise operate. For example, in the case of a lasso catheter, operating of the controls can deflect the lasso, and expand and contract the loop of the lasso. The distal end of the elongate medical device extends through the lumen of a sheath 464. The proximal end of the sheath 464 is engaged in the front clamp 174A of a second remote manipulator 50" which can be identical to manipulator 50, except that the second clamp 174B, which is unnecessary, has be removed. The distal end of the sheath 464 is bent or has some other shape to facilitate navigation, and the remote manipulator 50" can advance, retract, and rotate the sheath to navigate the distal end of the sheath in the body. The remote operator 50" and the remote operator 50 can be operated in coordinated manner so that the remote operator 50" brings the distal end of the sheath 464 to the desired location or orientation, and the remote manipulator 50 advances and retracts the medical device 462 through the lumen of the sheath and out the distal end, and operates the handle 460 to operate the distal end of the medical device.

Figure 46:
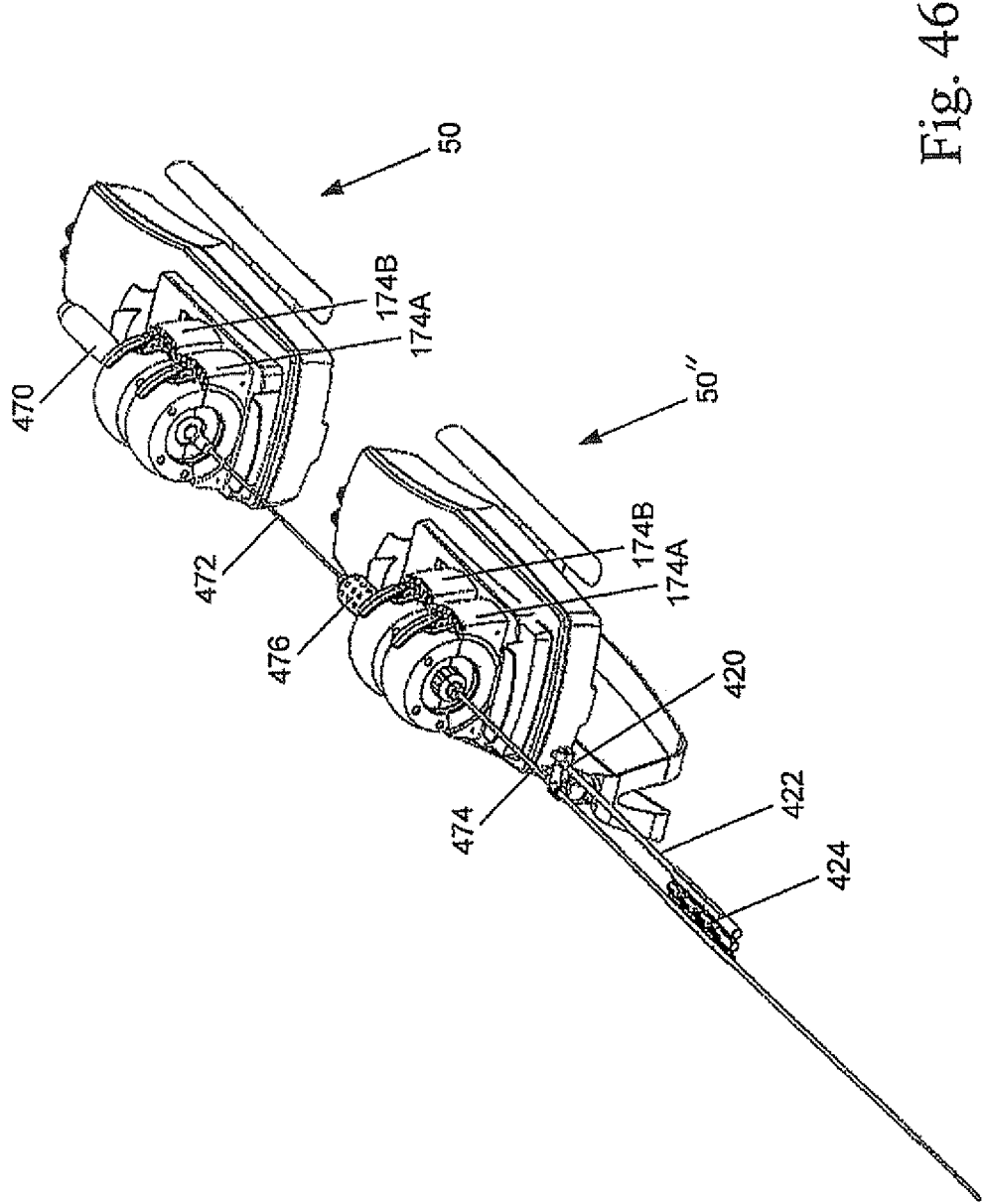
FIG. 46 is a perspective view of an alternate arrangement of the remote manipulator of the preferred embodiment for rotating, operating and advancing a manipulable sheath, and for operating and advancing an elongate medical device in the lumen of the manipulable sheath.
Figure 47:
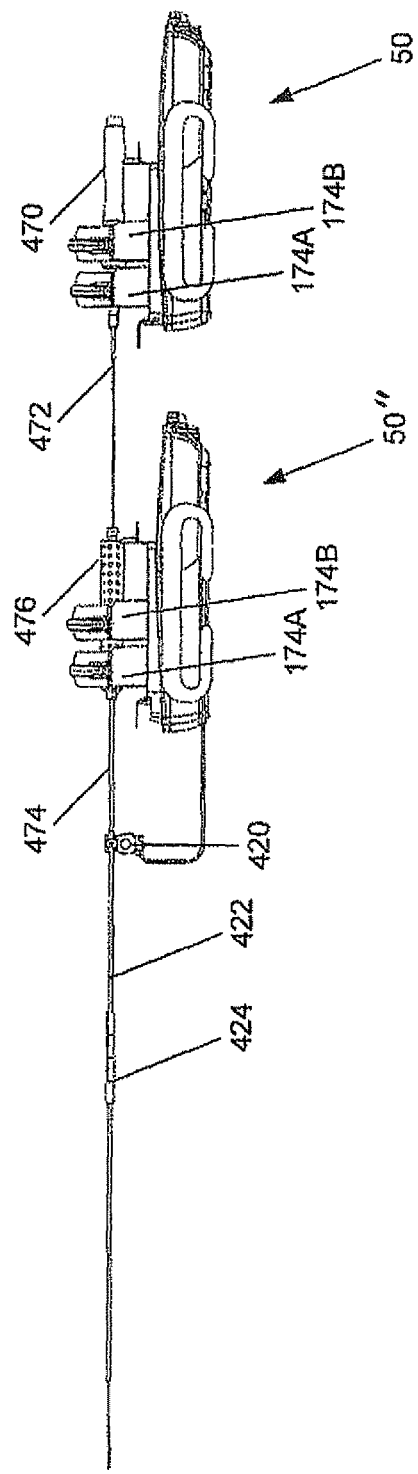
FIG. 47 is a side elevation view of an alternate arrangement of the remote manipulator of FIG. 46.

Another alternate arrangement of the remote manipulator of the preferred embodiment is shown in FIGS. 46 and 47 as it would arranged for rotating, operating and advancing a manipulable sheath and for operating and advancing and retracting a medical device in the lumen of the sheath. The remote manipulator 50 engages the handle 470 on the proximal end of a remotely manipulable medical device 472. The remote manipulator 50 can advance retract the medical device, and operate the controls on the handle 470 to cause the distal end of the medical device 472 to bend or other otherwise operate. For example, in the case of a lasso catheter, operating of the controls can deflect the lasso, and expand and contract the loop of the lasso. The distal end of the elongate medical device extends through the lumen of a sheath 474.

The remote manipulator 50" engages the handle 476 of the remotely manipulable sheath 474. The remote manipulator 50 can rotate, advance and retract the sheath 474 and operate the controls on the handle 476 to cause the distal end of the sheath to bend or turn. Thus the remote operators 50 and 50" can be operated in coordinated manner so one remote operator 50" brings the distal end of the sheath 474 to the desired location or orientation, and the remote manipulator 50 advances and retracts the medical device 472 through the lumen of the sheath and out the distal end, and operates the handle 470 to operate the distal end of the medical device. Thus the manipulable sheath 474 can be rotated, advanced and retracted, and operated, and a medical device 472 can be advanced and retracted through the lumen of the manipulable sheath, remotely.

Operation

The operation of the preferred embodiment will be described with respect to a loop type EP Catheter, although, the invention is not so limited and embodiments of the remote manipulator can be used to operate a wide variety of medical devices which can be controlled through the manipulation of handle. The medical device has a handle with an actuator ring. Rotation of the actuator ring relative to the remainder of the handle causes the distal end of the loop catheter to bend. Translation of the actuator ring relative to the remainder of the handle causes the ring at the distal end to increase or decrease in size.

Figure 37:
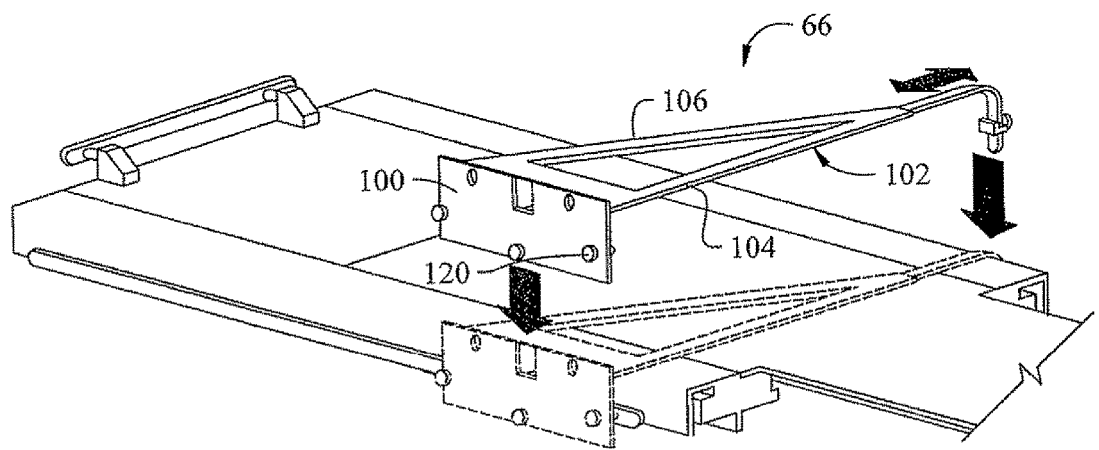
FIG. 37 is a perspective view showing the support installed on the bed.
Figure 38:
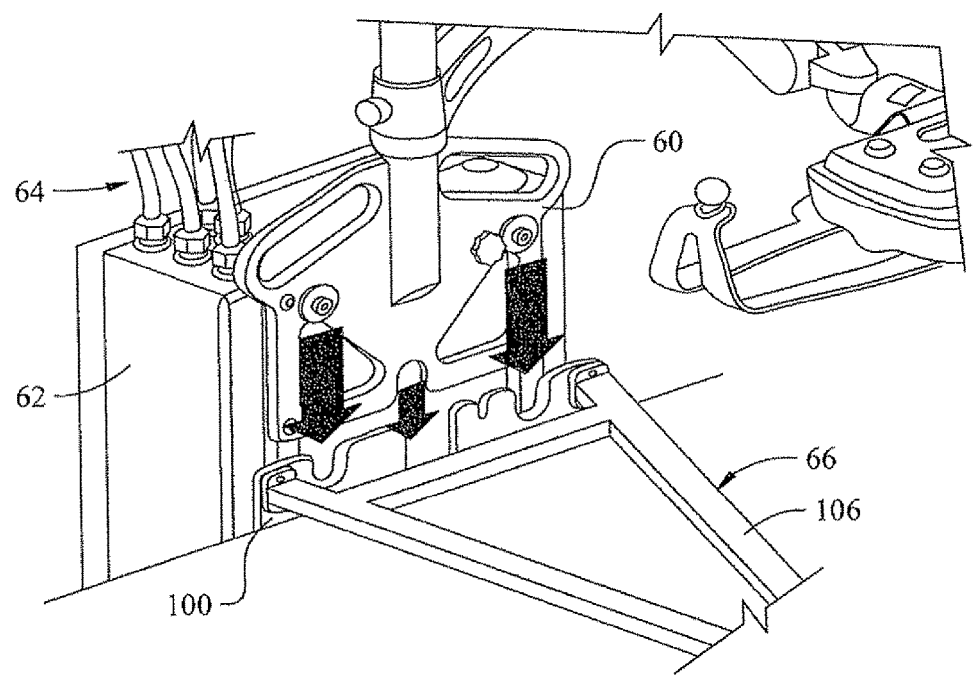
FIG. 38 is a perspective view showing the mounting of the bracket and controller on the base plate of the support.

The system is first installed on a patient bed. As shown in FIG. 37, the platform 66 is laid across the surface of the bed, and secured to rails found on the sides of a typical patient bed. The cleats on the 112 and 114 on the base plate 100 are secured to the rail on one side of the bed by tightening the bolts 120 and 122. Similarly, on the opposite side of the bed, the cleat 124 on L-shaped bracket 110 is secured to the rail by tightening the bolt 128. Once the platform 66 has been secured on the patient bed, the bracket 60 is mounted on the platform 66. As shown in FIG. 38, the pins 94 and 96 on the bracket 60 fit into the semi-circular notches 130 and 132 in the support plate 100, and the pin 134 on the plate 100 engages the semi-circular notch 98 in the bracket 60. The bracket 60 and the support plate are secured by tightening bolt 136 on the bracket to engage the slot 138 in the base plate.

The device driver 52 is then positioned in the appropriate location by pivoting the articulating arm 56 around post 58, and securing it with bolt 76. The sections 70 and 72 can be moved and driver device 52 can be pivoted about the first, second, and third axes to bring the driver device to an appropriate position for conducting the procedure.

A surgical drape (not shown) in the form of an elongate plastic bag can be installed over the device driver 52 and articulating arm 56. The drape preferably has a puncturable window that generally corresponds in size and shape to the platform 204, and is aligned therewith. A replaceable disposable device interface 54, which can be provided in a sterile package, is removed from its sterile packaging and installed on the platform 204 of the device driver 52, with the pins 226 and 228 and spline 230 of each of the clamps 174 piercing the drape to connect to the sockets in the driver device. Alternatively, the window in the drape can be a framed opening, the tray 220 can seal with the frame, and the pins 226 and 228, and the spline 230 can engage their respective sockets without interference from the drape.

Figure 39:
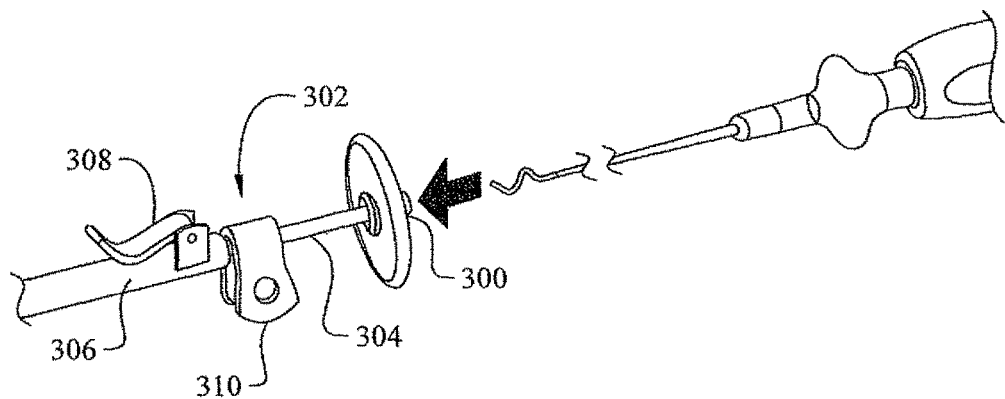
FIG. 39 is a perspective view of the proximal end of a telescoping catheter support.

The elongate medical device is then prepared for use and mounting in the remote manipulator system. As shown in FIG. 39, the distal end of the medical device is introduced into the opening 300 in the proximal end of a telescoping catheter support 302. The telescoping catheter support 302 comprises at least two relatively telescoping tubes 304 and 306 with a lock 308 for locking the tubes 304 and 306 in position to set the length of the support. The distal end of the support 302 engages the introducer sheath. A clip 310 allows the proximal end of the catheter support 302 to engage the mount 168, the spherical shape of the mount 168 helps form a ball joint with the clip 310 to accommodate some motion and realignment.

Figures 40A, 40B, 40C:
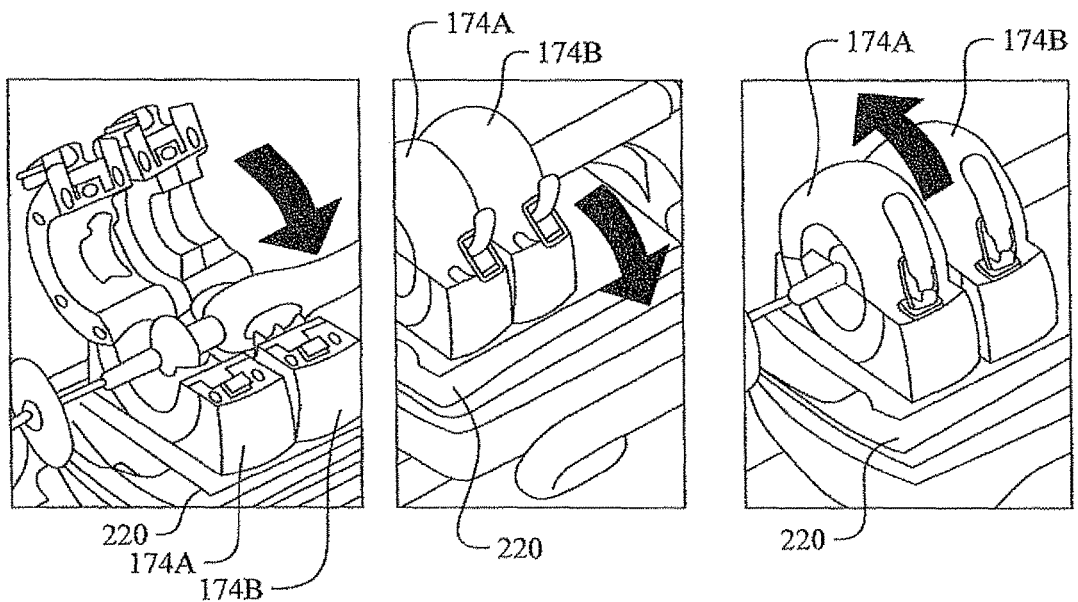
FIG. 40A is a perspective view of a medical device being placed in the clamps.
FIG. 40B is a perspective view of the covers of the clamps being closed over a medical device being placed in the clamps.
FIG. 40C is a perspective view of the covers of the clamps being latched to secure a medical device being placed in the clamps.

As shown in FIGS. 40A through 40C, the clamps 174A and 174B are opened, and the handle of the medical device placed in the clamps, with the actuator ring of the medical device aligned with clamp 174A, and the remainder of the handle aligned with clamp 1748. The covers 264 of the clamps 174A and 174B are closed, and the latches 270 engaged.

Once the medical device is engaged in the remote manipulator system, the distal end of the medical device can be introduced into the body and manipulated with the remote manipulation system 50.

When it is desired to advance the catheter, the drive 148 is actuated which causes the translation mechanism 212 to advance the body 170 of the device driver 52 relative to the base 160, which advances the catheter mounted thereon. When it is desired to retract the catheter, the drive 148 is actuated which causes the translation mechanism 212 to retract the body 170 of the device driver relative to its base 160. When it is desired to rotate the distal end of the catheter, the drives 142 and 146 are operated to operate transmissions 206 and 310 which cause the splines 230 of both of the clamps 174A and 174B to turn, thereby turning the split adapter ring gears 302 and thus, the entire device engaged therein. When it is desired to operate the actuation ring on the handle of the device, relative translation of the ring and the remainder of the handle can be caused by operating the drive 144 to operate the translation mechanism 208 to cause the clamp 174B engaging the handle to move relative to the clamp 174A engaging the actuator ring, to thereby cause relative movement between the actuator ring and the handle. Relative rotation of the actuator ring and the remainder of the handle can be caused by operating the drive 142 to operate transmission 206 to operate the spline 230 of clamp 174A, rotating the actuator ring relative to the remainder of the handle, or operating drive 210 to operate transmission 210 to operate the spline 230 of clamp 174B rotating the remainder of the handle relative to the actuator ring, or to operate drives 142 and 146 and different rates and or in different directions to cause relative rotation between the actuator ring engaged in clamp 174A and the remainder of the handle engaged in 174B.

The drives 142, 144, 146, and 148 can be under direct control by a physician through a suitable interface, or the drives can be under the control of a microprocessor under the supervision and direction of a physician.

In an emergency, the clamps 174A and 174B can be easily opened by operating latches 270 to release the cover and pulling the medical device free. The split adapter rings can be easily removed from the device so that the device can be used manually.

Embodiments of the remote manipulator device can be adapted to a wide variety of medical devices to allow the devices to be positioned and operated inside the body under remote control by a physician, or by physician-supervised computer control.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

What is claimed is:

1. A system for operating a delivery sheath for a medical device and a medical device delivered through the delivery sheath, the delivery sheath having a distal end adapted to be navigated in the body, and a proximal end having a handle with a translatable control and a rotatable control for acting on the distal end of the delivery sheath, and a lumen extending through the delivery sheath and the handle for the passage of a medical device therethrough, and the medical device being adapted to extend through the lumen in the delivery sheath and out the distal end, the system comprising:

a releasable clamp for engaging the handle of the delivery sheath;

a socket for receiving and engaging the releasable clamp on the handle of the delivery sheath;

a translation mechanism for advancing and retracting the socket to advance and retract the delivery sheath whose handle is received in the clamp engaged in the socket;

a rotation mechanism for rotating the socket to rotate the delivery sheath whose handle is received in the clamp engaged by the socket;

a translation operator for engaging the translatable control on the handle of the delivery sheath whose handle is received in the clamp and operating the translatable control relative to the handle to act on the distal end of the delivery sheath;

a rotation operator for engaging the rotatable control of the delivery sheath whose handle is received in the clamp and operating the rotatable control relative to the handle to act on the distal end of the delivery sheath; and a medical device advancer for engaging and advancing the medical device at least partly disposed in the lumen of delivery sheath.

2. The system according to claim 1 wherein the advancer is top loading to allow the medical device to be introduced into and removed from the advancer at any point intermediate its proximal and distal ends.

3. A system for operating a delivery sheath for a medical device and a medical device delivered through the sheath, the delivery sheath having a distal end adapted to be navigated in the body, and a proximal end having a handle with a translatable control and a rotatable control for acting on the distal end of the delivery sheath, and a lumen extending through the delivery sheath and handle for the passage of a portion of the medical device therethrough, and the medical device adapted to extend through the lumen of the sheath and having a distal end adapted to be navigated in the body, and a proximal end having a handle with a translatable control and a rotatable control for acting on the distal end of the medical device, the system comprising:

a delivery sheath controller comprising:

a first releasable clamp for engaging the handle of the delivery sheath;

a first socket for receiving and engaging the first releasable clamp on the handle of the delivery sheath;

a first translation mechanism for advancing and retracting the first socket to advance and retract the delivery sheath whose handle is received in the first clamp engaged in the first socket;

a first rotation mechanism for rotating the first socket to rotate the delivery sheath whose handle is received in the first clamp engaged in the first socket;

a first translation operator for engaging the translatable control of the delivery sheath whose handle is received in the first clamp engaged in the first socket and operating the translatable control relative to the handle to act on the distal end of the delivery sheath; and a first rotation operator for engaging the rotatable control of the delivery sheath whose handle is received in the first socket and operating the rotatable control relative to the handle to act on the distal end of the delivery sheath; and a medical device controller comprising:

a second releasable clamp for engaging the handle of the medical device;

a second socket for receiving and engaging the second releasable clamp on the handle of the medical device;

a second translation mechanism for advancing and retracting the second socket to advance and retract the medical device whose handle is received in the second releasable clamp engaged by the second socket;

a second rotation mechanism for rotating the second socket to rotate the medical device whose handle is received in the second releasable clamp engaged by the second socket;

a second translation operator for engaging the translatable control of the medical device whose handle is received in the second releasable clamp engaged in the second socket and operating the translatable control relative to the handle of the medical device to act on the distal end of the medical device; and a second rotation operator for engaging the rotatable control of the medical device whose handle is received in the second releasable clamp engaged in the second socket and operating the rotatable control relative to the handle of the medical device to act on the distal end of the medical device.

* * * * *